United States Patent
Syed

(10) Patent No.: US 10,568,829 B2
(45) Date of Patent: Feb. 25, 2020

(54) HAIR RELAXER COMPOSITIONS AND METHOD

(71) Applicant: AVLON INDUSTRIES, INC., Melrose Park, IL (US)

(72) Inventor: Ali N. Syed, Oakbrook, IL (US)

(73) Assignee: Avlon Industries, Inc., Melrose Park, IL (US)

( * ) Notice: Subject to any disclaimer, the term of this patent is extended or adjusted under 35 U.S.C. 154(b) by 0 days.

(21) Appl. No.: 16/086,514

(22) PCT Filed: May 5, 2017

(86) PCT No.: PCT/US2017/031296
§ 371 (c)(1),
(2) Date: Sep. 19, 2018

(87) PCT Pub. No.: WO2017/192990
PCT Pub. Date: Nov. 9, 2017

(65) Prior Publication Data
US 2019/0046431 A1     Feb. 14, 2019

Related U.S. Application Data

(60) Provisional application No. 62/332,066, filed on May 5, 2016.

(51) Int. Cl.
| | | |
|---|---|---|
| *A61K 8/898* | (2006.01) | |
| *A61K 8/06* | (2006.01) | |
| *A61K 8/19* | (2006.01) | |
| *A61K 8/41* | (2006.01) | |
| *A61K 8/43* | (2006.01) | |
| *A61Q 5/04* | (2006.01) | |

(52) U.S. Cl.
CPC .............. *A61K 8/898* (2013.01); *A61K 8/068* (2013.01); *A61K 8/19* (2013.01); *A61K 8/416* (2013.01); *A61K 8/43* (2013.01); *A61Q 5/04* (2013.01)

(58) Field of Classification Search
CPC ...................................................... A61Q 5/04
See application file for complete search history.

(56) References Cited

U.S. PATENT DOCUMENTS

| | | |
|---|---|---|
| 2003/0049222 A1 | 3/2003 | Akhter et al. |
| 2003/0232910 A1 | 12/2003 | McDermott et al. |
| 2011/0020249 A1* | 1/2011 | Lorentz ................. A61K 8/898 424/54 |
| 2015/0004112 A1 | 1/2015 | Ritter et al. |

FOREIGN PATENT DOCUMENTS

WO       2011089985 A1    7/2011

OTHER PUBLICATIONS

SAAPEDIA, Propoxytetramethyl piperidinyl dimethicone, Accessed Sep. 30, 2019, URL: http://www.saapedia.org/en/saa/?type=detail&id=5090 (Year: 2019).*
Mintel, anonymous: "One Week Straightener", XP055622596, www.gnpd.com, Database Accession No. 573472.
Anonymous, "wow, Temporary Relaxer!!!"/Long Hair Care Forum, pp. 1-6, XP055622653, Dec. 27, 2006, www.longhaircareforum.com/threads/wow-temporary-relaxer, 110807.
Communication, Extended European Search, dated Dec. 2, 2019.

* cited by examiner

*Primary Examiner* — Bethany P Barham
*Assistant Examiner* — Barbara S Frazier
(74) *Attorney, Agent, or Firm* — Olson & Cepuritis, Ltd.

(57) ABSTRACT

Disclosed is a fiber elasticity conserving hair relaxer composition having an alkalinity of at least pH 12 comprising a fiber elasticity conserving amount of at least one hair fiber elasticity conserving agent selected from the group consisting of poly-organosiloxanes containing, per molecule, at least one siloxyl unit substituted with at least one group having one or more of a sterically hindered piperidinyl functional group. The composition substantially ameliorates the loss of hair fiber elasticity that frequently occurs during the hair relaxing step of a process for relaxing the natural curl of hair under such strongly alkaline conditions.

14 Claims, No Drawings

HAIR RELAXER COMPOSITIONS AND METHOD

CROSS-REFERENCE TO RELATED APPLICATIONS

This application is a 371 National Stage of International Application No. PCT/US2017/031296, filed May 5, 2017, which claims the benefit of U.S. Provisional Patent Application No. 62/332,066, filed May 5, 2016, each application being incorporated herein by reference in its entirety.

FIELD OF THE INVENTION

This invention relates to the chemical straightening or relaxing of human hair under strongly alkaline conditions, and in particular to ameliorating the loss in hair fiber elasticity that often occurs during such process.

BACKGROUND OF THE INVENTION

Commercial alkaline chemical relaxers for straightening naturally wavy and curly hair, sometimes called "textured hair," under strongly alkaline conditions (pH≥12) generally use either an alkali metal hydroxide, or a strong organic base as the active ingredient. Conventional alkali metal hydroxide containing relaxers typically contain sodium hydroxide as the active alkali and are commonly called "lye-type" relaxers. Conventional organic base containing relaxers typically contain guanidine hydroxide as the active alkali and are commonly called "no-lye-type" relaxers. Sodium hydroxide and guanidine hydroxide are generally preferred for effectively achieving a desirable level of straightening under strongly alkaline conditions.

A drawback of a sodium hydroxide, lye-type relaxer is its higher potential for irritation of the scalp during the hair straightening process as compared to a guanidine hydroxide, no-lye type relaxer. An advantage of a sodium hydroxide, lye-type relaxer is that it is a single component system, i.e., the active alkali is an ingredient in the composition and is ready to use. Guanidine hydroxide has a relatively short stability in solution, so a guanidine hydroxide, no-lye type relaxer is a two-component system comprising a cream base and a liquid "activator" that must be mixed together to form guanidine hydroxide in situ. The ingredients of the cream base component are primarily oils, such as petrolatum/mineral oil, emulsifiers, and calcium hydroxide. The liquid activator generally is a solution of guanidine carbonate in water. For use, the cream and liquid activator are mixed together typically at a ratio of about 3.75 to 1 and the freshly made mixture is applied substantially immediately to the curly hair.

A drawback of commercial hair relaxers containing either sodium hydroxide or guanidine hydroxide as the active alkali is that a loss of fiber elasticity can result generally reducing the elasticity of wet fibers by about 35 to about 60 percent, typically at least about 50 percent. Loss of wet fiber elasticity is undesirable and is believed to manifest itself as fiber breakage when the fiber is dry, especially on combing.

There is a need and desire for an alkaline hair relaxer system that substantially conserves fiber elasticity and ameliorates loss of fiber elasticity during the hair relaxing process under strongly alkaline conditions (pH≥12).

SUMMARY OF THE INVENTION

Disclosed is a hair relaxer or straightening composition having an alkalinity of at least pH 12 comprising at least one hair fiber elasticity conserving agent in an aqueous cosmetically acceptable vehicle, and method for ameliorating the loss of hair fiber elasticity that frequently occurs during the hair relaxing step of the process of straightening the natural curl of hair under such strongly alkaline conditions.

The hair fiber elasticity conserving agent is preferably selected from the group consisting of polyorganosiloxanes containing, per molecule, at least one siloxyl unit substituted with at least one group having one or more of a sterically hindered piperidinyl functional group. Particularly preferred polyorganosiloxanes are compounds having at least one siloxyl unit substituted with a pendant side chain comprising a 2,2,6,6-tetramethylpiperidinyl group, preferably attached to the silicon as represented by general Formula (I).

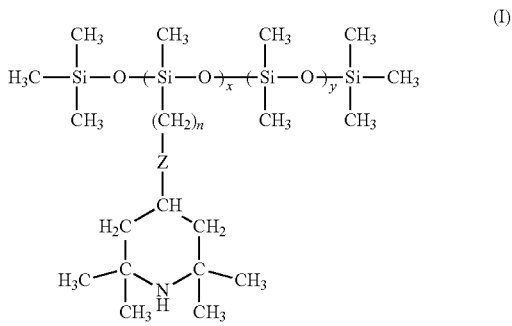

where the average value of x and y each is independently 1 to about 200, preferably 1 to about 50; n is 0, 1, 2 or 3, preferably 3; and Z is a heteroatom or substituted heteroatom, e.g., O, NR (where R is H or alkyl), and S, preferably Z is O (oxygen).

In a particularly preferred embodiment, the polysiloxane component comprises a propyloxytetramethyl piperidinyl group of Formula (II).

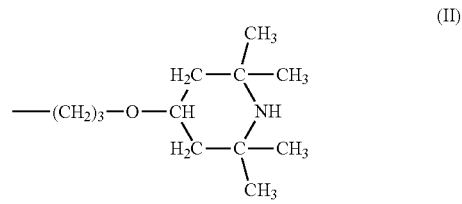

A preferred polyorganosiloxane having a Formula II component is commercially identified by the INCI name: propoxytetramethyl piperidinyl dimethicone, referred to herein as PPDM, for convenience.

As described in detail hereafter, the loss in wet hair fiber elasticity which typically occurs during the process of relaxing hair with a strongly alkaline conventional hair relaxer (pH 12-14) was found to be substantially ameliorated by the presence of the fiber elasticity conserving agent, propoxytetramethyl piperidinyl dimethicone (PPDM), in the hair relaxer. Amelioration in loss of wet hair fiber elasticity was assessed by measuring the tensile strength of the hair fiber before and after relaxation with a strongly alkaline hair relaxer using an Intermittent Stress Relaxation (ISR) Method generally described in Method Section I and I-A. Additionally, amelioration in loss of hair fiber elasticity from relaxation with a strongly alkaline hair relaxer was assessed by a decrease in hair breakage of dry relaxed hair following multiple brushings using the Brushing/Combing Method generally described in Method Section II.

Surprisingly, a greater conservation of hair fiber elasticity was noted when the PPDM was present in a no-lye type guanidine hydroxide hair relaxer relative to that achieved when the PPDM was present in a lye-type sodium hydroxide hair relaxer.

DETAILED DESCRIPTION OF THE INVENTION

The singular terms "a", "an", and "the", as used in the specification and the appended claims include plural referents unless the context clearly dictates otherwise. The antecedent term "about" applied to a recited range or value denotes an approximation within the deviation in the range or value known or expected in the art from the measurements method. Recitation of ranges of values herein are merely intended to serve as a shorthand method of referring individually to each separate value falling within the range, unless otherwise indicated herein, and each separate value is incorporated into the specification as if it were individually recited herein.

The terms "hair fiber elasticity" and "hair fiber tensile strength" are used interchangeably herein to define the ability of a hair fiber to recover from mechanical deformation from stress/strain, while wet or dry, or resist breakage on combing or brushing. The term "hair fiber elasticity conservation" and grammatical variations thereof as applied to a hair fiber elasticity conserving agent means that loss in hair fiber elasticity (i.e., loss in tensile strength) that typically occurs during the process of straightening the hair under strongly alkaline conditions (pH≥12) is ameliorated or diminished by the presence of the agent (i.e., compound or compounds) in the hair relaxing composition. Thus, a hair fiber elasticity conserving agent discernibly and significantly conserves and preserves more of the pre-relaxed, tensile strength of the hair fiber, when the agent is present relative to the tensile strength of the hair fiber when the agent is not present. Wet hair fiber elasticity was measured by the Method I described below, but is not intended to be limited thereto. Dry hair fiber elasticity was measured by Method II described below, but is not intended to be limited thereto.

A preferred hair fiber elasticity conserving agent is a polyorganosiloxane. Polyorganosiloxanes are compounds containing pendant side chain components attached to the Si of a siloxyl unit, the various pendent units being randomly distributed in the siloxane chain. A particularly preferred side chain component is "hindered amine" group.

Useful polyorganosiloxanes contain, per molecule, at least one siloxyl unit substituted with at least one group having one or more of a sterically hindered piperidinyl functional group. Descriptions of useful polyorganosiloxanes bearing hindered amine groups are found in U.S. Pat. Nos. 8,481,014, and 6,642,194, the relevant disclosures of which are each incorporated herein by reference.

Preferred polyorganosiloxanes are compounds having at least one siloxyl unit substituted with a pendant side chain comprising a 2,2,6,6-tetramethylpiperidinyl group, preferably attached to the silicon as represented by general Formula (I).

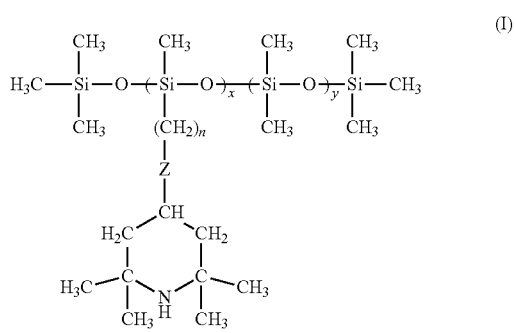

where the average value of x and y each is independently 1 to about 200, preferably 1 to about 50; n is 0, 1, 2 or 3, preferably 3; and Z is a heteroatom or substituted heteroatom, e.g., O, NR (where R is H or alkyl), and S, preferably Z is O (oxygen).

In a particularly preferred embodiment, the polysiloxane component comprises a propyloxytetramethyl piperidinyl group of Formula (II).

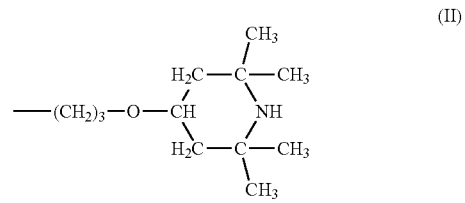

A preferred polyorganosiloxane having a Formula II component is commercially identified by the INCI name: propoxytetramethyl piperidinyl dimethicone, referred to herein as PPDM, for convenience.

According to the manufacturers, propoxytetramethyl piperidinyl dimethicone (PPDM) has a reported molecular weight of about 10,000 to about 100,000, and an amine (N) content of about 2,500 to about 3780 ppm at room temperature. Propoxytetramethyl piperidinyl dimethicones are supplied as fluids, varying in viscosity in a range of from about 5 to about 100,000 cps (mPa·s), or in the form of emulsions comprising the polyorganosiloxane. The term "emulsions" as used herein with reference to polyorganosiloxanes, such as propoxytetramethyl piperidinyl dimethicone, encompasses macroemulsions, miniemulsions or microemulsions thereof, which are in a thermodynamically stable state. Useful propoxytetramethyl piperidinyl dimethicones are sold by Chemsil Silicones Inc. under the tradenames, DIMETHISIL and MICROSIL, supplied, respectively, as 100% active PPDM oils or as aqueous micro-emulsions, available in fluid viscosities varying from about 5 to about 90,000 mPa·s; sold by Bluestar Silicones under the tradename MIRASIL as medium to high viscosity fluids, as a 50% active propoxytetramethyl piperidinyl dimethicone in C15-19 alkane fluid, and as an aqueous emulsion of 25% propoxytetramethyl piperidinyl dimethicone and trideceth-6; and sold by Jeen International Corporation under the JEESILC UAF trademark as a fluid having a reported viscosity of about 10,000-60,000 mPa·s.

Microemulsions of PPDM preferably contain at least one quaternary ammonium compound. Preferred quaternary ammonium compounds without being limited thereto, include cetyl trimethylammonium bromide (INCI: Cetrimonium Bromide); cetyl trimethylammonium chloride (INCI: Cetrimonium Chloride); stearyl trimethylammonium bromide (INCI: Steartrimonium Bromide); stearyl trimethyl ammonium chloride (INCI: Steartrimonium Chloride) and the like.

Commercial microemulsions preferably include synthetic or natural alkanes or alkoxylated alcohols having about 10 to about 20 carbon atoms in the alkyl chain. For example, microemulsions containing PPDM sold under the tradename MICROSIL contain C11-C15 Pareth-7, which is the INCI name for a polyethylene glycol ether of a mixture of synthetic C11-15 fatty alcohols with an average of 7 moles of ethylene oxide and Trideceth-6 which is the INCI name for a polyethylene glycol ether of tridecyl alcohol having an average value of 6 moles of ethylene oxide.

The fiber elasticity conserving agent, PPDM, preferably is present at an active concentration in the range of about 0.1 to about 4 weight percent; more preferably in the range of about 0.5 to about 3.5 weight percent; and most preferably in the range of about 0.9 to about 3.2 weight percent, based on the total weight of the hair relaxer composition applied to the hair.

The terms "relax" and "straighten," and grammatical variations thereof with reference to hair are used interchangeably herein to mean that the natural curl or wave pattern of the hair has been chemically straightened to a substantially straight configuration by lanthionization with an alkaline composition having a pH of at least 12. The term "hair relaxer composition" as used herein includes a composition commonly referred to as a "hair straightener". The term "permanent straightening" means that the natural curl of the hair has been chemically removed to a visually discernible straight configuration that effectively resists reversion (i.e., resumption of a curly pattern) on being subjected to more than one washing, and preferably lasts until the naturally curly scalp hair portion grows sufficiently to visually warrant another hair straightening procedure. The terms "washed" and "washing" includes rinsing with water.

Those skilled in the hair relaxing arts will appreciate that strongly alkaline hair relaxing compositions having a pH in the range of pH 12 to about 14 typically are formulated in the form of a viscous emulsion cream, (called cream base), or a non-slurry emulsion comprising a cosmetically acceptable vehicle. The term "cosmetically acceptable vehicle" means that the composition comprises water and ingredients commonly recognized in the art as suitable for compositions, such as cosmetics, cosmeceuticals, and the like, that are topically applied to human hair and skin.

Cosmetically acceptable vehicles used for hair straightening compositions in the form of aqueous emulsion cream are primarily comprised of lipophilic oleaginous ingredients, such as oils, petrolatum, and mineral waxes, and emulsifiers into which the active hair relaxing alkaline ingredient is incorporated. Examples of useful aqueous cosmetically acceptable vehicles for the practice of this invention are illustrated in the Examples below, without being limited thereto.

Ingredients and optional cosmetic adjuvants that can be included in the hair relaxer compositions discussed herein are referred to by their commonly used chemical or trade names or by the international nomenclature commonly referred to as INCI name given them in any edition of the International Cosmetic Ingredient Dictionary and Handbook, (hereafter INCI Dictionary), such as found in Volumes 1-3, of the Seventh Edition (1997) or Eighth Edition (2000) or Ninth Edition (2002), all published by the Cosmetic, Toiletry, and Fragrance Association, Washington D.C. (now Personal Care Products Council). Numerous commercial suppliers of materials listed by INCI name, trade name, or both, can be found in any edition of the INCI Dictionary and in numerous commercial trade publications, including but not limited to, the 2001 *Cosmetic Bench Reference edition of COSMETICS & TOILETRIES®*, 115 (13), or the *Cosmetic Bench Reference* 2004, both published by Allured Publishing Corporation, Carol Stream, Ill. (2001), and the 2001 McCutcheon's Directories, Volume 1: Emulsifiers & Detergents and Volume 2: Functional Materials, published by McCutcheon's Division, The Manufacturing Confectioner Publishing Co., Glen Rock, N.J. (2001); the relevant disclosures of each of the foregoing publications being incorporated herein by reference.

The term "cosmetic adjuvant" includes cosmetically useful product finishing and promotional additives, well known and conventionally used in the cosmetic arts to maintain the physical stability (shelf life), and the visible aesthetic appearance of a composition during storage and during the use of the composition. Cosmetic adjuvants that maintain the stability of products typically include a metal-ion chelating agent, an antioxidizing agent, a preservative, an emulsifying agent, a perfume solubilizer, and the like, but are not limited thereto. Cosmetic adjuvants, sometimes called promotional ingredients, aid in enhancing the aesthetics and marketing appeal of the product and include, without limitation, a product colorant, a fragrance, and the like.

The active hair relaxing ingredient in conventional hair relaxer products is a strong chemical base preferably comprising at least one compound selected from the group consisting of an alkali metal hydroxide, an alkaline earth metal hydroxide, an organic amine, and water soluble alkaline salts thereof. In hair relaxer compositions commonly known in the art as no-base, lye-type hair relaxers the active hair relaxing ingredient is generally an alkali metal hydroxide. Preferred alkali metal hydroxides are selected from the group consisting of sodium hydroxide, potassium hydroxide, and lithium hydroxide. Sodium hydroxide is preferred and can be present in amounts from about 1 to about 4 weight percent, preferably from about 1.5 to about 3 weight percent, more preferably from about 2 to about 2.5 weight percent, based on the total weight of the composition applied to the hair.

In hair relaxer compositions commonly known in the art as no-base, no-lye type hair relaxers, the active hair relaxing ingredient is a strong organic base. Strong organic amines are preferably guanidine compounds (e.g. guanidine or derivatives thereof). Preferred guanidine compounds include guanidine, guanidine hydroxide, and water soluble alkaline guanidine salts from which free guanidine can be liberated in situ. A useful active hair relaxing amount of strong organic base is in the range of about 3 to about 8 percent by weight, based on the total weight of the composition applied to the hair.

No-lye type guanidine hydroxide hair relaxers are preferably prepared just before use by admixing a first composition comprising an alkaline earth metal hydroxide with a separately prepared second composition comprising a water soluble, alkaline salt of guanidine to liberate an effective hair straightening amount of guanidine hydroxide in situ. Alkaline earth metal hydroxides are selected from the group consisting of calcium hydroxide, barium hydroxide and strontium hydroxide. Calcium hydroxide is preferred. Alkaline, water-soluble guanidine salts are selected from the group consisting of guanidine carbonate, guanidine sulfate, and guanidine sulfite. Guanidine carbonate is preferred. Conventionally a no-lye type hair relaxer is prepared from a cream base composition portion comprising about 4 to about 8 percent, preferably about 5.5 to about 7.5 weight percent, calcium hydroxide and a liquid "activator" portion comprising about 24 to about 29 percent, preferably about 25 to about 28 weight percent, guanidine carbonate in water. For use, the cream base and liquid activator are mixed together typically at a ratio of about 3.75 to 1 and the freshly made mixture is applied substantially immediately to the curly hair.

At least one hair fiber elasticity conserving agent can be present as an ingredient of the highly alkaline relaxer cream applied to the hair. Where a no-lye type, guanidine hydroxide relaxer is used, the hair fiber elasticity conserving agent can be present in either the alkaline relaxer cream base portion, in the liquid activator portion, or in both the alkaline relaxer cream base and the liquid activator portions during manufacture or can be added as a separate component during the admixture of the cream base and activator. Where a highly alkaline lye-type relaxer cream containing alkali metal hydroxide as the active hair straightening agent is used, the hair fiber elasticity conserving agent can be present as an ingredient in the cream during manufacture.

When hair fibers are damaged, they typically show combing and brushing fatigue and break during grooming. Thus, a combing/brushing technique was judged realistically useful for examining the mildness or aggressiveness of chemical treatments toward hair fibers. For example, as reported by McMichael, "Hair Breakage in Normal and Weathered Hair: Focus on the Black Patient", *Journal of Investigative Dermatology Symposium Proceedings* 12, p. 6-9 (2007), hair fiber breakage is a large problem in many individuals and is especially significant in African American patients. When fibers are treated with chemical relaxers based on guanidine hydroxide or sodium hydroxide as active hair straightening ingredients, the fibers may tend to break easily upon combing and brushing and consumers become alarmed when they see many broken hair fibers in the brush or comb.

Combing and brushing as a measure of hair damage has been studied and reported using equipment where hair tresses are combed repeatedly using a rotating hollow drum-like assembly where outer crossbars contain holders for mounting combs or brushes. The brushes or combs are mounted at 90° angles, allowing one complete drum revolution to brush a stationary tress and the procedure is repeated four times. Collection plates are located under each tress to collect broken fiber fragments, while spacer plates on the rotating drum prevent cross contamination. A description of such a device is found in Ch. 8, "Hair breakage", *Practical Modern Hair Science*. Ed. Evans & Wickett. Allured Publishing Corp., Carol Stream, Ill., p. 281, (2012); and in Evans, T. A. and Park, K., "A statistical analysis of hair breakage II: Repeated grooming experiments", *Journal of Cosmetic Science*, Vol. 61, 439-455, (2010). Evans reported that the combination of size and shape of hair tresses, the tooth spacing of the brush or comb, the condition of the hair, and the humidity dictates the magnitude of grooming stress and the breakage. The resistance of hair fibers to repeated combing/brushing has also been studied and reported by others using a technique called Flexabrasion, described by Swift et al., "Flexabrasion: A Method for Evaluating Hair Strength" *Cosmetics & Toiletries*, Vol. 116, No. 12, 53-58 (December, 2001).

In a hair-breakage method embodiment, chemically relaxed dry hair fibers were combed repeatedly using a commonly used salon brush and the broken fibers were collected and counted to compare the effectiveness of fiber elasticity conserving agents in various hair relaxer treatments. This brushing simulated practical grooming conditions where consumers brushed their hair with about 200 to 300 strokes over a period of 3 months, as reported, for example, by Dubief, C., et al., in Chapter 4 "Hair Care Products" in *The Science of Hair Care*. Ed: Claude Nouillon and John Wilkinson, Taylor & Francis, Boca Raton, Fla., p. 144, (2005).

In the following non-limiting examples the following materials and methods were used, unless otherwise indicated, to assess the efficacy of a hair fiber elasticity conserving agent in ameliorating loss of hair fiber elasticity during an alkaline hair straightening process. One preferred method determined fiber elasticity by mechanically measuring tensile strength based on stress applied to wet fibers at a constant strain of 0.5%; another preferred method measured elasticity based on the amount of hair fiber breakage noted during repetitive combing/brushing.

Materials and Methods
Materials

The following fiber elasticity conserving agents used are cationic silicone fluids, reportedly having about 2,500-3,780 ppm N, having the INCI name and commercial tradename below as provided by the commercial supplier, Chemsil Silicones, Inc.

DIMETHISIL HNH-HV: INCI: Propoxytetramethyl Piperidinyl Dimethicone, a 100% active oil, reportedly having a fluid viscosity of about 90,000 mPa·s at 25° C., and an amine content of 2500 ppm, referred to herein as high viscosity PPDM.

DIMETHISIL HNH-MV: INCI: Propoxytetramethyl Piperidinyl Dimethicone, a 100% active oil, reportedly having a fluid viscosity of about 10,000 mPa·s at 25° C., and an amine content of 2500 ppm, referred to herein as medium viscosity PPDM.

DIMETHISIL HNH-LV: INCI: Propoxytetramethyl Piperidinyl Dimethicone, a 100% active oil, reportedly having a fluid viscosity of about 250 mPa·s at 25° C., and an amine content of 3780 ppm referred to herein as low viscosity PPDM.

MICROSIL HAF-HV: INCI: Propoxytetramethyl Piperidinyl Dimethicone (and) C11-C15 Pareth-7 (and) Trideceth-6, supplied as an aqueous, submicron emulsion reportedly comprising about 25-30% Propoxytetramethyl Piperidinyl Dimethicone, (DIMETHISIL HNH-HV), about 0.3-1% C11-C15 Pareth-7 and about 4.9-10% Trideceth-6; and reportedly has a pH of 4-6, a 0.010 micron mean particle size and a viscosity of less than 200 mPa·s at 25° C.

MICROSIL HAF-MV-30: INCI: Propoxytetramethyl Piperidinyl Dimethicone (and) C11-15 Pareth-7 (and) Trideceth-6, supplied as an aqueous, submicron emulsion reportedly comprising about 25-30% Propoxytetramethyl Piperidinyl Dimethicone, (DIMETHISIL HNH-MV), about 0.3-1% C11-C15 and about 4.9-10% Trideceth-6 and reportedly has a pH of 4-6, a 0.010 micron mean particle size, and a viscosity of less than 200 mPa·s at 25° C.

MICROSIL VOLUME: INCI: Propoxytetramethyl Piperidinyl Dimethicone (and) Cetrimonium Chloride (and) C11-C15 Pareth-7 (and) Trideceth-6, supplied as an aqueous, submicron emulsion reportedly comprising about 15-20% Propoxytetramethyl Piperidinyl Dimethicone (DIMETHISIL-MV); about 1-5% cetrimonium chloride, about 1-3% C11-C15 Pareth-7 and about 5-10% Trideceth-6. MICROSIL VOLUME reportedly has a pH of 4-7 and is water soluble.

MICROSIL FINISH: INCI: Propoxytetramethyl Piperidinyl Dimethicone (and) Cetrimonium Chloride (and) Cetrimonium Bromide (and) Trideceth-6 (and) C11-C15 Pareth- 7, supplied as an aqueous, submicron o/w emulsion reportedly comprising about 7-12% Propoxytetramethyl Piperidinyl Dimethicone (DIMETHISIL HNH-HV) about 5-10% cetrimonium chloride, about 4-9% cetrimonium bromide, about 2-7% Trideceth-6 and about 0.5-2% C11-C15 Pareth-7. MICROSIL FINISH reportedly has a pH of 5-6 and is insoluble in water.

Methods

I. Intermittent Stress Relaxation Method (ISR)

One preferred method of evaluating the elastic tensile strength (fiber elasticity) of wet hair is referred to as the "Intermittent Stress Relaxation (ISR) Method" using a Dynamic Mechanical Analyzer (e.g., TA Instruments, Model Q800) equipped with a hair-fiber anchoring assembly that can be submerged in water. In the intermittent stress relaxation (ISR) method the hair is probed (stretched) with a short pulse of force, (tension applied) followed by a period of recovery during which the hair is not subjected to any tension. In the ISR method, a single fiber, about 7-inches long (gauge length=14.82 millimeters (mm)) is mounted to the submersible fiber specimen clamp and submerged in water. The wet fiber is stretched (probed) to a constant strain or 0.5% of its length (from 14.82 to 14.89 mm length) for 1 second and allowed to recover for about 59 seconds. This process cycle of imposing the strain and allowing it to recover is repeated for a total of 10 cycles. The force is expressed in grams while the area is expressed in denier (a textile terminology defined as weight in grams of 9,000 meters of yarns or fibers). The area of the hair specimen is measured using a LaserMike® scanning micrometer (Beta LaserMike, USA). The average area is recorded as (x+y)/2 where x is the minor axis and y the major axis. The amount of stress (in grams/denier fiber) for each cycle of hair fiber is measured and recorded before and after receiving a hair straightening procedure. The ratio (index) of the stress force of the hair before receiving the procedure relative to the stress force of the hair after the procedure is calculated and the change in the ratio is judged as indicative of loss, or protection from loss, in wet tensile strength (fiber elasticity).

In the following Examples, the ISR value was evaluated for randomly sampled ten to twelve hair fibers by measuring the wet ISR value of each hair fiber (after 10 cycles) before and after a hair straightening procedure and then calculating the ISR Index in this manner for each of the sampled fibers. The ISR procedure was conducted on the same hair fiber immersed in water (100% relative humidity (RH)), first before the relaxer process, and second after the relaxer process as described in Section I-A. The calculated ratio of the wet ISR value after-to-before the relaxer (ISR Index) was used to assess the internal condition of hair fibers. A calculated ISR Index of 1.0 indicated that there was no chemical damage done to the hair (i.e., no chemical change in tensile strength). A calculated ISR Index of less than 1.0 suggested that fibers were chemically damaged internally indicating a loss in tensile strength. A preferred general hair relaxer/ISR procedure is described in section I-A below.

Measuring the elasticity of wet hair, when stretched in the range of about 0.5 to about 1 percent of its length, is judged as simulating the range of strain applied during a conventional hair grooming process, such as combing, brushing, styling and setting of the hair.

A. Hair Relaxer/ISR Procedure.

For the purpose of illustrating the efficacy of the fiber elasticity conserving agents, Caucasian straight hair was used because it has the least amount of diameter variability across the fiber hair shaft. Caucasian hair was obtained from reputable hair suppliers, such as IMHAIR, Italy or DeMeo Brothers in New York. The wet ISR values of the selected hair fibers was measured before the relaxer process and the pre-tested hair fibers were then embedded into a 7-inch, 2 gram tress of Caucasian hair for the relaxer procedure. A hair relaxer composition (about 8 grams) was applied to the tress. The hair relaxer was left on the tress for about 18 minutes, then removed by water rinsing the tress thoroughly for about 3 minutes and then towel-blotting the rinsed tress. The rinsed, blotted tress was then washed with about 2.5 grams of acidic neutralizing shampoo for about 3 minutes, water rinsed for about 3 minutes, and the washing step was repeated for a total of two washings. The relaxed fibers were then equilibrated overnight at ambient room temperature and a relative humidity of about 60%. The wet ISR values were again determined for the pre-selected fibers after the relaxation procedure.

II. Hair Combing Breakage Method

In order to mimic real life hair fatigue and hair breakage from repeated grooming, i.e. multiple combing and brushing, a combing/brushing device was constructed generally similar to the device pictured and described in Practical Modern Hair Science by Evans, in Chapter 8 supra. Dry hair tresses were repeatedly brushed for up to 1200 times, and the number of fibers broken upon brushing were collected and counted. The difference in broken fibers collected after repeated brushing of hair receiving a relaxer procedure with relaxer containing fiber elasticity conserving agent was compared to those of hair receiving a procedure with a comparative relaxer control (without fiber elasticity conserving agent). A description of the combing/brushing device follows.

The combing/brushing device consisted of a motorized arm capable of revolving in a circular motion and a stationary arm having a tress holder. The motorized arm was equipped with a salon-style brush (Pivot Point 207, 9-row air forming brush having nylon bristles spaced apart at 0.5 centimeters) anchored at both ends. A 4-gram, 7-inch hair tress was attached to the stationary arm of the device and the hair tress was positioned in the path of the motorized arm. This way the scalp to end portion of the stationary tress was brushed at a selected speed by the motorized arm to which a selected brush is attached. A collection plate was positioned underneath the hair tress being brushed and collected any of the fibers broken during brushing.

Four hair tresses were used for each hair relaxer evaluated. Multiple brushings in incremental amounts of 400 strokes were performed up to a total of at least 1200 brushing strokes or more. After the completion of 400 brushing strokes, the broken fibers from the collection plate underneath the tress and broken fibers entangled with the brush were collected and counted. A decrease in the number of broken fibers achieved with a hair relaxer containing fiber elasticity conserving agent relative to the number of broken fibers using a comparative hair relaxer control was judged to indicate amelioration in loss of fiber elasticity, and hence as reflecting protection from fiber breakage and decrease in hair fatigue. The number of broken fibers for each relaxer procedure were statistically compared using software SPSS from IBM.

A brushing of about 1200 times reportedly simulates the approximate number of brushings/combing strokes an individual may have performed for a period of one year. See, for example, Dubief, et al., Hair Care Products in *The Science of Hair Care*. supra.

Example 1. Comparative Guanidine Hydroxide Relaxer

This comparative example illustrates the effect of a conventional guanidine hydroxide relaxer system on the fiber elasticity of hair.

A set of hair fibers was relaxed with a conventional, two-part, no-lye type, guanidine hydroxide relaxer system. One part (Part A) of the relaxer was a non-conditioning, commercial alkaline relaxer cream base, (Sensitive Scalp, Avlon, Inc.), having the formula shown in Table 1, and the other part, (Part B), was a commercial, non-conditioning conventional liquid activator, (AFFIRM, Avlon, Inc.) having the formula shown in Table 2.

TABLE 1

Conventional Relaxer Cream Base

| Ingredient (Common/Trade Name/INCI Name) | Weight % (as supplied) |
|---|---|
| 1. Petrolatum | 23 |
| 2. Mineral oil | 13.5 |
| 3. Emulsifying wax NF (Note a) | 11 |
| 4. LANETH-15 (Note b) | 1 |
| 5. PEG-75 Lanolin (Note c) | 0.5 |
| 6. Water | 43.5 |
| 7. Propylene glycol | 2 |
| 8. Calcium hydroxide | 5.5 |
| pH = 12.5; Viscosity = 52,000 mPa · s | |

Footnotes to Table 1.
(Note a) Nonionic emulsifier prepared from cetostearyl alcohol containing a polyoxyethylene derivative of a fatty acid ester of sorbitan commercially available under the trade names POLAWAX (Croda, Inc.) and LIPOWAX P (Lipo Chemicals, Inc.
(Note b) INCI name for a polyethylene glycol ether of lanolin alcohol having an average ethoxylation value of 15 commercially available under the trade name POLYCHOL-15 (Croda, Inc.).
(Note c) INCI name for a polyethylene glycol derivative of lanolin having an average of 75 moles of ethylene oxide commercially available under the trade name SUPER SOLAN (Croda, Inc.).

The cream base composition was prepared as follows: An oil phase was prepared containing ingredients 1-4 heated to a range of 78-80° C., mixing until homogeneous. An aqueous solution of ingredient 8 was prepared using a sufficient portion of the water (ingredient 6). A separate water phase was prepared containing ingredients 5, 7 and the remaining amount of ingredient 6 heated to a range of 78-80° C., mixing until homogeneous. The oil phase was then added to the water phase at a temperature of 78-80° C., and mixed together with stirring agitation for about 15 minutes using a LIGHTENING mixer. The resulting emulsion was then cooled to a temperature of about 50° C. and the aqueous solution of ingredient 8 was added and homogeneously mixed together. The batch was then cooled to a temperature of about 25° C., under stirring agitation using a sweep mixer (KITCHEN AID mixer). The product was then manually homogenized using a hand held homogenizer. The calcium hydroxide content was calculated by titration method and the viscosity was measured using a BROOKFIELD Viscometer.

TABLE 2

Conventional Liquid Activator

| Ingredient (Common/Trade Name/INCI Name) | Weight % (As Supplied) |
|---|---|
| Water, deionized, to 100% | q.s. |
| Xanthan gum (Note a) | 0.25 |
| Disodium EDTA (Note b) | 0.2 |
| Guanidine carbonate | 27.2 |
| Product colorant | q.s. |
| pH = 11.26; Viscosity = 780 mPa · s | |

Footnotes to Table 2.
q.s. = quantity sufficient
(Note a) INCI name for thickener commercially available under the trade name KELTROL CG.
(Note b) INCI name for ethylenediamine tetraacetic acid, disodium salt, dihydrate commercially available under the trade name DISSOLVINE Na2-S.

Just before use, the relaxer cream base of Table 1 (Part A) was mixed with the liquid activator of Table 2 (Part B) at a ratio of about 3.78:1 to provide guanidine hydroxide relaxer 1A shown in Table 3.

TABLE 3

Comparative Guanidine Hydroxide Relaxer 1A

| Component in Mixture | (%)Weight |
|---|---|
| Part A: Relaxer Cream Base of Table 1 | 79.1 |
| Part B: Liquid Activator of Table 2 | 20.9 |
| pH = 13.1 | |

The general hair relaxer/ISR procedure described in Section IA above was followed using ten preselected hair fibers and the ISR values were determined before and after relaxation. For the relaxation procedure, freshly prepared guanidine hydroxide Relaxer cream 1A of Table 3 was applied to the hair for a relaxation period of about 18 minutes. The relaxed hair was water rinsed and then shampooed twice with a conventional non-conditioning Neutralizing Shampoo having the formula shown in Table 4.

TABLE 4

Conventional Neutralizing Shampoo

| Ingredient (Common/Trade Name/INCI Name) | % Weight (As supplied) |
|---|---|
| Water to 100% final | q.s |
| Disodium EDTA | 0.2 |
| Ammonium lauryl sulfate | 10 |
| Cocamide DEA (Note a) | 4.5 |
| Citric Acid | 0.45 |
| Product colorant | q.s. |
| Preservative | q.s. |
| pH = 4.5; Viscosity 1700 mPa · s | |

Footnote to Table 4.
(Note a) INCI Name for coconut diethanolamide commercially available under the trade name MACKAMIDE BY-23.

The shampooed, relaxed fibers were then allowed to air dry at ambient room temperature overnight. The ISR value of the pre-selected relaxed ten fibers was determined by the ISR Method I described above. The wet ISR values before and after relaxer treatment and the calculated ISR Index for the 10 fibers relaxed with the comparative guanidine hydroxide relaxer are shown in Table 5.

TABLE 5

ISR Data for Fibers Relaxed with Comparative Guanidine Hydroxide Relaxer 1A

| Fiber No. | ISR Value Before Relaxer 1A | ISR Value After Relaxer 1A | Calculated ISR Index |
|---|---|---|---|
| 1 | 12.39 | 7.03 | 0.57 |
| 2 | 14.1 | 5.43 | 0.39 |
| 3 | 11.98 | 3.17 | 0.26 |
| 4 | 11.9 | 5.47 | 0.46 |
| 5 | 10.82 | 4.51 | 0.42 |
| 6 | 13.4 | 4.72 | 0.35 |
| 7 | 13.81 | 4.16 | 0.30 |
| 8 | 12.97 | 6.43 | 0.50 |
| 9 | 15.42 | 5.17 | 0.34 |
| 10 | 12.85 | 5.1 | 0.40 |
| Average | 12.96 | 5.12 | 0.40 |
| S.D.* | 1.30 | 1.10 | 0.09 |
| COV (%)** | 10.05 | 21.44 | 23.44 |

Footnoted to Table 5.
*S.D. = Standard Deviation;
**COV = Coefficient of Variance.

The ISR Data show that on average, the comparative conventional guanidine hydroxide Relaxer 1A decreased the wet fiber elasticity tensile strength of the hair about 60% based on a calculated average ISR Index of 0.4.

Example 2. Fiber Elasticity Conserving Guanidine Hydroxide Relaxer

This example illustrates the amelioration in loss of wet hair fiber elasticity during hair relaxation with a no-lye type, guanidine hydroxide relaxer when a hair fiber elasticity conserving agent, proproxytetramethyl piperidinyl dimethicone (PPDM) was present at an active concentration in the range of about 0.9 to about 3.5%. Three different concentrations of fiber elasticity conserving agent were evaluated and wet fiber elasticity was measured by the ISR Method I at 100% RH as described above.

No-lye type, guanidine hydroxide relaxers were prepared containing, as the fiber elasticity conserving agent, a high viscosity PPDM, DIMETHISIL HNH-HV, at a concentration, as supplied, of about 0.97% (Relaxer 2A); of about 2.1% (Relaxer 2B); and of about 3.2% (Relaxer 2C). DIMETHISIL HNH-HV is the tradename for material having the INCI name: Propoxytetramethyl Piperidinyl Dimethicone having a high viscosity as described above in the Materials section. The composition of Relaxers 2A, 2B, and 2C are shown in Table 6.

TABLE 6

Guanidine Hydroxide Relaxer with Fiber Elasticity Conserving Agent Propoxytetramethyl Piperidinyl Dimethicone (PPDM)

| Component | Relaxer 2A Wt. % | Relaxer 2B Wt. % | Relaxer 2C Wt. % |
|---|---|---|---|
| Part A: Relaxer Cream Base of Table 1 | 78.13 | 77 | 75.9 |
| Part B: Liquid Activator of Table 2 | 20.9 | 20.9 | 20.9 |
| Part C: DIMETHISIL HNH-HV | 0.97 | 2.1 | 3.2 |
| pH = | 14.1 | 13 | 14.3 |

The fiber elasticity conserving guanidine hydroxide Relaxers, 2A, 2B, and 2C, were each prepared by mixing together the components shown in Table 6 substantially immediately before using on the hair. The hair relaxer procedure of Example 1 was followed except that a first set of 12 hair fibers was relaxed with Relaxer 2A; a separate second set of 12 fibers was relaxed with Relaxer 2B and a separate third set of 12 fibers was relaxed with Relaxer 2C of Table 6. The ISR Data for the fibers relaxed with the hair Relaxer 2A is shown in Table 7; with the hair Relaxer 2B is shown in Table 8; and with the hair Relaxer 2C is shown in Table 9.

TABLE 7

ISR Data for Fibers Relaxed with the Fiber Elasticity Conserving Guanidine Hydroxide Relaxer 2A

| Fiber No. | ISR Value Before Relaxer 2A | ISR Value After 2A Relaxer | Calculated ISR Index |
|---|---|---|---|
| 1 | 63.73 | 38.88 | 0.61 |
| 2 | 57.67 | 34.55 | 0.60 |
| 3 | 55.73 | 45.18 | 0.81 |
| 4 | 70.41 | 47.25 | 0.67 |
| 5 | 70.37 | 51.99 | 0.74 |
| 6 | 57.68 | 28.64 | 0.50 |
| 7 | 61.55 | 42.20 | 0.69 |
| 8 | 69.02 | 45.39 | 0.66 |
| 9 | 54.72 | 46.28 | 0.85 |
| 10 | 43.51 | 26.88 | 0.62 |
| 11 | 51.11 | 23.20 | 0.45 |
| 12 | 69.92 | 42.48 | 0.61 |
| Average | 60.45 | 39.41 | 0.65 |
| S.D. | 8.62 | 9.11 | 0.11 |
| COV (%) | 14.26 | 23.11 | 17.58 |

TABLE 8

ISR Data for Fibers Relaxed with the Fiber Elasticity Conserving Guanidine Hydroxide Relaxer 2B

| Fiber No. | ISR Value Before Relaxer 2B | ISR Value After 2B Relaxer | Calculated ISR Index |
|---|---|---|---|
| 1 | 60.95 | 47.41 | 0.78 |
| 2 | 65.53 | 55.67 | 0.85 |
| 3 | 71.04 | 51.48 | 0.72 |
| 4 | 54.07 | 45.83 | 0.85 |
| 5 | 65.68 | 48.51 | 0.74 |
| 6 | 67.14 | 58.10 | 0.87 |
| 7 | 59.44 | 43.04 | 0.72 |
| 8 | 77.12 | 66.05 | 0.86 |
| 9 | 64.96 | 55.17 | 0.85 |
| 10 | 63.95 | 54.69 | 0.86 |
| 11 | 52.52 | 44.75 | 0.85 |
| 12 | 66.24 | 54.92 | 0.83 |
| Average | 64.05 | 52.13 | 0.81 |
| S.D. | 6.48 | 6.31 | 0.05 |
| COV (%) | 10.11 | 12.11 | 6.59 |

TABLE 9

ISR Data for Fibers Relaxed with the Fiber Elasticity Conserving Guanidine Hydroxide Relaxer 2C

| Fiber No. | ISR Value Before Relaxer 2C | ISR Value After Relaxer 2C | Calculated ISR Index |
|---|---|---|---|
| 1 | 64.44 | 35.67 | 0.55 |
| 2 | 58.32 | 29.71 | 0.51 |
| 3 | 37.04 | 32.46 | 0.88 |
| 4 | 49.57 | 30.32 | 0.61 |
| 5 | 63.27 | 50.07 | 0.79 |
| 6 | 56.09 | 39.04 | 0.70 |
| 7 | 44.57 | 39.50 | 0.89 |
| 8 | 57.20 | 50.55 | 0.88 |
| 9 | 63.20 | 44.64 | 0.71 |

TABLE 9-continued

ISR Data for Fibers Relaxed with the Fiber Elasticity Conserving Guanidine Hydroxide Relaxer 2C

| Fiber No. | ISR Value Before Relaxer 2C | ISR Value After Relaxer 2C | Calculated ISR Index |
|---|---|---|---|
| 10 | 64.21 | 49.09 | 0.76 |
| 11 | 69.96 | 51.28 | 0.73 |
| 12 | 51.00 | 36.76 | 0.72 |
| Average | 56.57 | 40.76 | 0.73 |
| S.D. | 9.52 | 8.11 | 0.12 |
| COV (%) | 16.83 | 19.91 | 17.07 |

The ISR data for the hair relaxers, 2A, 2B, and 2C, were statistically compared against one another and against the ISR data obtained with the comparative hair Relaxer 1A of Example 1, using an ANOVA Tukey B test. Based on the differences in the calculated average ISR index, the amelioration in loss of hair fiber elasticity achieved with hair Relaxer 2B>hair Relaxer 2C>hair Relaxer 2A and these differences were judged significant at p<0.05. The data surprisingly showed that the fiber elasticity conserving agent was more effective at a concentration of 2.1% than at a concentration of 3.2%.

The increase in the average ISR index data of the three fiber elasticity conserving Relaxers 2A (0.65), 2B (0.81) and 2C (0.73) was judged statistically higher relative to that of the comparative hair Relaxer 1A of Example 1 (0.40). Based on the calculated average ISR indices, this represented a reduction in the % loss of wet fiber elasticity from about 60% (control Relaxer 1A) to about 35% by Relaxer 2A, to about 18% by Relaxer 2B and to about 27% by Relaxer 2C. Thus, the increased calculated average ISR index of hair relaxed with Relaxers 2A, 2B and 2C relative to the calculated ISR Index of the comparative conventional guanidine hydroxide Relaxer 1A of Example 1 indicated that a significant amount of hair fiber elasticity was conserved by the presence of high viscosity, proproxytetramethyl piperidinyl dimethicone at a active concentration in the range of 0.97 to 3.2% in the hair relaxer.

Example 3. Fiber Elasticity Conserving Guanidine Hydroxide Relaxer

This example illustrates the amelioration in loss of hair fiber elasticity during hair relaxation with a no-lye type, guanidine hydroxide relaxer when a hair fiber elasticity conserving agent, proproxytetramethyl piperidinyl dimethicone was present in the form of sub-micron emulsion form. Three different concentrations of fiber elasticity conserving agent were evaluated and wet fiber elasticity was measured by the ISR Method I described above.

No-lye type, guanidine hydroxide relaxers were prepared containing, as the fiber elasticity conserving agent, MICROSIL HAF-HV sub-micron emulsion, present in the hair relaxer, at a concentration, as supplied, of about 3.2% (Relaxer 3A); of about 7% (Relaxer 3B); and of about 10.7% (Relaxer 3C). As described above, MICROSIL HAF-HV is the tradename for the material having the INCI name: Propoxytetramethyl Piperidinyl Dimethicone (and) C11-15 Pareth-7 (and) Trideceth-6, and was supplied as an aqueous, submicron emulsion of about 30% propoxytetramethyl piperidinyl dimethicone, (DIMETHISIL HNH-HV). Thus the active concentration of the fiber elasticity conserving agent, propoxytetramethyl piperidinyl dimethicone (PPDM), used in Relaxer 3A was about 0.97%; in Relaxer 3B was about 2.1%; and in Relaxer 3C was about 3.2%. The composition of Relaxers 3A, 3B and 3C are shown in Table 10.

TABLE 10

Guanidine Hydroxide Relaxer with Fiber Elasticity Conserving Agent Propoxytetramethyl Piperidinyl Dimethicone (PPDM)

| Component | Relaxer 3A Wt. % | Relaxer 3B Wt. % | Relaxer 3C Wt. % |
|---|---|---|---|
| Part A: Relaxer Cream Base of Table 1 | 75.9 | 72.1 | 68.4 |
| Part B: Liquid Activator of Table 2 | 20.9 | 20.9 | 20.9 |
| Part C: MICROSIL HAF-HV (30% PPDM) | 3.2 | 7 | 10.7 |

The guanidine hydroxide Relaxers, 3A, 3B, and 3C, were prepared by mixing together the components shown in Table 10 substantially immediately before using on the hair. The hair relaxer procedure of Example 1 was followed except that a first set of hair fibers was relaxed with Relaxer 3A; a separate second set was relaxed with Relaxer 3B and a separate third set was relaxed with Relaxer 3C of Table 10.

The ISR Data for the fibers relaxed with the hair Relaxer 3A is shown in Table 11; with the hair Relaxer 3B is shown in Table 12; and with the hair Relaxer 3C is shown in Table 13.

TABLE 11

ISR Data for Fibers Relaxed with Fiber Elasticity Conserving Guanidine Hydroxide Relaxer 3A

| Fiber No. | ISR Value Before Relaxer 3A | ISR Value After Relaxer 3A | Calculated ISR Index |
|---|---|---|---|
| 1 | 62.24 | 39.99 | 0.64 |
| 2 | 73.01 | 58.77 | 0.81 |
| 3 | 52.59 | 43.47 | 0.83 |
| 4 | 65.46 | 57.00 | 0.87 |
| 5 | 71.73 | 61.28 | 0.85 |
| 6 | 66.32 | 57.68 | 0.87 |
| 7 | 60.34 | 48.13 | 0.80 |
| 8 | 49.42 | 29.76 | 0.60 |
| 9 | 50.27 | 43.70 | 0.87 |
| 10 | 53.12 | 37.83 | 0.71 |
| Average | 60.45 | 47.76 | 0.79 |
| S.D. | 8.75 | 10.57 | 0.10 |
| COV (%) | 14.47 | 22.13 | 12.64 |

TABLE 12

ISR Data for Fibers Relaxed with Fiber Elasticity Conserving Guanidine Hydroxide Relaxer 3B

| Fiber No. | ISR Value Before Relaxer 3B | ISR Value After Relaxer 3B | Calculated ISR Index |
|---|---|---|---|
| 1 | 67.55 | 37.19 | 0.55 |
| 2 | 75.33 | 36.67 | 0.49 |
| 3 | 61.38 | 33.23 | 0.54 |
| 4 | 62.14 | 35.58 | 0.57 |
| 5 | 52.76 | 35.13 | 0.67 |
| 6 | 51.62 | 27.79 | 0.54 |
| 7 | 66.46 | 38.33 | 0.58 |
| 8 | 44.38 | 27.21 | 0.61 |
| 9 | 39.96 | 27.34 | 0.68 |
| 10 | 42.04 | 23.36 | 0.56 |
| Average | 56.36 | 32.18 | 0.58 |
| S.D. | 12.01 | 5.27 | 0.06 |
| COV (%) | 21.31 | 16.37 | 10.48 |

TABLE 13

ISR Data for Fibers Relaxed with Fiber Elasticity
Conserving Guanidine Hydroxide Relaxer 3C

| Fiber No. | ISR Value Before Relaxer 3C | ISR Value After Relaxer 3C | Calculated ISR Index |
|---|---|---|---|
| 1 | 64.61 | 34.58 | 0.54 |
| 2 | 56.78 | 32.87 | 0.58 |
| 3 | 69.16 | 24.09 | 0.35 |
| 4 | 52.87 | 25.74 | 0.49 |
| 5 | 60.00 | 37.24 | 0.62 |
| 6 | 47.20 | 23.26 | 0.49 |
| 7 | 51.09 | 27.84 | 0.54 |
| 8 | 40.85 | 19.58 | 0.48 |
| 9 | 61.09 | 36.98 | 0.61 |
| 10 | 41.21 | 24.14 | 0.59 |
| Average | 54.49 | 28.63 | 0.53 |
| S.D. | 9.58 | 6.30 | 0.08 |
| COV (%) | 17.59 | 22.02 | 15.28 |

The ISR data for the hair Relaxers, 3A, 3B, and 3C, were statistically compared against one another and against the ISR data obtained with the comparative hair Relaxer 1A of Example 1, using an ANOVA Tukey B test. Based on the differences in average ISR index, the amelioration in loss of hair fiber elasticity achieved with hair Relaxer 3A>hair Relaxer 3B>hair Relaxer 3C and these differences were judged significant at p=<0.05.

The increase in the average ISR index data of the three fiber elasticity conserving Relaxers 3A (0.79), 3B (0.58) and 3C (0.53) was judged statistically higher relative to that of the comparative hair Relaxer 1A of Example 1 (0.40). Based on the calculated average ISR indices, this represented a reduction in the % loss of wet fiber elasticity from about 60% (control Relaxer 1A) to about 21% by Relaxer 3A; to about 40% by Relaxer 3B; and to about 47% by Relaxer 3C. Thus, the increase in the average ISR index of hair relaxed with Relaxers 3A, 3B and 3C relative to the comparative conventional guanidine hydroxide Relaxer 1A of Example 1 indicated that a significant amount of hair fiber elasticity was conserved by the presence of high-viscosity proproxytetramethyl piperidinyl dimethicone in the form of a microemulsion at an active PPDM concentration in the range of about 0.97 to about 3.2% in the hair relaxer.

Example 4. Comparative Alkali Metal Hydroxide Hair Relaxer

This comparative example illustrates the loss in hair fiber elasticity from a conventional lye-type, alkali metal hydroxide hair relaxer containing sodium hydroxide at an active concentration in the range of about 2 to 2.5 weight %. A conventional, lye-type, hair Relaxer 4A having the composition shown in Table 14 was prepared.

TABLE 14

Comparative Sodium Hydroxide Hair Relaxer 4A

| Ingredient (Common/Tradename/INCI Name) | % Weight (As supplied) |
|---|---|
| 1. Petrolatum | 23 |
| 2. Mineral oil | 13.5 |
| 3. Emulsifying wax N.F. | 11 |
| 4. LANTH-15 | 1 |
| 5. PEG-75 LANOLIN | 0.5 |
| 6. Water to 100% | q.s |

TABLE 14-continued

Comparative Sodium Hydroxide Hair Relaxer 4A

| Ingredient (Common/Tradename/INCI Name) | % Weight (As supplied) |
|---|---|
| 7. Propylene glycol | 2 |
| 8. Sodium hydroxide | 2.2 | pH = 13.5;
Viscosity = 34,000-54,000 mPa · s.

The comparative hair relaxer of Table 14 was prepared as an emulsion cream as follows: An oil phase was prepared containing ingredients 1-4 heated to a temperature of about 78-80° C. A concentrated aqueous solution of about 50% active ingredient 8 was prepared with a portion of ingredient 6. A water phase containing ingredients 5, 7 and the remaining amount of ingredient 6 was prepared and heated to a temperature of about 78-80° C. The oil phase was added to the water phase at a temperature of about 78-80° C. and mixed together with stirring agitation for about 15 minutes, using a LIGHTENING mixer to produce an emulsion. The emulsion was cooled to about 50° C. and the aqueous sodium hydroxide was added and the batch was then cooled to about 25° C., using a sweep mixer (KITCHEN AID mixer). The cooled batch was then manually homogenized using a hand-held homogenizer. The sodium hydroxide content was then calculated by acid-base titration and the viscosity was measured using a BROOKFIELD viscometer.

The general Hair Relaxer/ISR procedure described in Section I-A was followed using the comparative Sodium Hydroxide Hair Relaxer 4A of Table 14 and the conventional Neutralizing Shampoo of Table 4. The ISR data for 12 selected hair fibers before and after the Relaxer 4A procedure and the calculated ISR Index are shown in Table 15.

TABLE 15

ISR Data For Fibers Relaxed with Comparative
Sodium Hydroxide Relaxer 4A

| Fiber No. | ISR Value Before Relaxer 4A | ISR Value After Relaxer 4A | Calculated ISR Index |
|---|---|---|---|
| 1 | 86.75 | 40.93 | 0.47 |
| 2 | 85.41 | 50.78 | 0.59 |
| 3 | 63.24 | 39.13 | 0.62 |
| 4 | 56.23 | 43.63 | 0.78 |
| 5 | 66.60 | 47.55 | 0.71 |
| 6 | 63.57 | 39.75 | 0.63 |
| 7 | 73.94 | 32.45 | 0.44 |
| 8 | 80.11 | 51.33 | 0.64 |
| 9 | 55.90 | 49.78 | 0.89 |
| 10 | 61.61 | 34.64 | 0.56 |
| 11 | 63.35 | 37.28 | 0.59 |
| 12 | 60.25 | 35.73 | 0.59 |
| Average | 68.08 | 41.90 | 0.63 |
| S.D. | 10.82 | 6.62 | 0.12 |
| COV (%) | 15.90 | 15.80 | 19.77 |

The ISR data show that, on average, the comparative sodium hydroxide hair relaxer decreased the wet fiber elasticity (tensile strength) of the hair about 37% to a calculated average ISR Index of 0.63.

Example 5. Fiber Elasticity Conserving Alkali Metal Hydroxide Relaxer

This example illustrates the amelioration in loss of fiber elasticity from an alkali metal hydroxide, (lye-type), hair relaxer containing sodium hydroxide at an active concentration in the range of about 2 to 3.5 weight % when the fiber-elasticity conserving agent propoxytetramethyl piperidinyl dimethicone PPDM is present.

Lye-type, sodium hydroxide relaxers were prepared containing, as the fiber elasticity conserving agent a high viscosity PPDM, DIMETHISIL HNH-HV, at a concentration, as supplied, of about 0.97% (Relaxer 5A); of about 2.1% (Relaxer 5B); and of about 3.2% (Relaxer 5C). The compositions of hair Relaxers 5A, 5B, and 5C are shown in Table 16. The relaxer creams were prepared as described in Example 4, except that after the oil phase and water phase were mixed together to form the emulsion, the emulsion was cooled to a temperature of about 55° C. and the fiber elasticity agent (ingredient 9) was added and mixed for about 5 minutes before proceeding with the cooling step and addition of the sodium hydroxide.

The general Hair Relaxer/ISR procedure described in section I-A was followed using each one of hair Relaxers 5A, 5B and 5C. The ISR values of 15 selected fibers determined before and after the individual Relaxer treatment and the calculated ISR Index obtained with hair Relaxer 5A are shown in Table 17; with hair Relaxer 5B are shown in Table 18; and with hair Relaxer 5C are shown in Table 19.

TABLE 16

Fiber Conserving Sodium Hydroxide Hair Relaxer with Propoxytetramethyl Piperidinyl Dimethicone (PPDM)

| Ingredient (Common/Tradename/INCI Name) | % Weight (As supplied) Relaxer 5A | % Weight (As supplied) Relaxer 5B | % Weight (As supplied) Relaxer 5C |
| --- | --- | --- | --- |
| 1. Petrolatum | 23 | 23 | 23 |
| 2. Mineral oil | 13.5 | 13.5 | 13.5 |
| 3. Emulsifying wax N.F. | 11 | 11 | 11 |
| 4. LANETH-15 | 1 | 1 | 1 |
| 5. PEG-75-LANOLIN | 0.5 | 0.5 | 0.5 |
| 6. Water to 100% | q.s. | q.s. | q.s. |
| 7. Propylene glycol | 2 | 2 | 2 |
| 8. Sodium hydroxide | 2.2 | 2.2 | 2.2 |
| 9. DIMETHISIL HNH-HV | 0.97 | 2.1 | 3.2 |

TABLE 17

ISR Data for Fibers Relaxed with Fiber Elasticity Conserving Sodium Hydroxide Relaxer 5A

| Fiber No. | ISR Value Before Relaxer 5A | ISR Value After Relaxer 5A | Calculated ISR Index |
| --- | --- | --- | --- |
| 1 | 62.67 | 46.49 | 0.74 |
| 2 | 66.69 | 44.33 | 0.66 |
| 3 | 65.53 | 34.62 | 0.53 |
| 4 | 61.25 | 38.43 | 0.63 |
| 5 | 66.80 | 52.52 | 0.79 |
| 6 | 57.62 | 52.46 | 0.91 |
| 7 | 43.65 | 39.09 | 0.90 |
| 8 | 52.92 | 36.72 | 0.69 |
| 9 | 62.75 | 45.69 | 0.73 |
| 10 | 50.49 | 32.42 | 0.64 |
| 11 | 59.44 | 35.88 | 0.60 |
| 12 | 56.04 | 25.15 | 0.45 |
| 13 | 78.15 | 47.45 | 0.61 |
| 14 | 65.04 | 53.93 | 0.83 |
| 15 | 44.35 | 38.28 | 0.87 |
| Average | 59.56 | 41.57 | 0.71 |
| S.D. | 9.12 | 8.28 | 0.14 |
| COV (%) | 15.31 | 19.91 | 19.30 |

TABLE 18

ISR Data for Fibers Relaxed with Fiber Elasticity Conserving Soldium Hydroxide Relaxer 5B

| Fiber No. | ISR Value Before Relaxer 5B | ISR Value After Relaxer 5B | Calculated ISR Index |
| --- | --- | --- | --- |
| 1 | 55.64 | 32.65 | 0.59 |
| 2 | 76.75 | 54.75 | 0.71 |
| 3 | 56.44 | 33.93 | 0.60 |
| 4 | 49.00 | 36.97 | 0.75 |
| 5 | 62.96 | 40.49 | 0.64 |
| 6 | 68.30 | 45.46 | 0.67 |
| 7 | 71.19 | 44.73 | 0.63 |
| 8 | 74.99 | 47.20 | 0.63 |
| 9 | 64.21 | 41.92 | 0.65 |
| 10 | 51.14 | 35.07 | 0.69 |
| 11 | 62.45 | 28.03 | 0.45 |
| 12 | 57.25 | 26.57 | 0.46 |
| 13 | 70.44 | 47.17 | 0.67 |
| 14 | 69.54 | 58.24 | 0.84 |
| 15 | 62.07 | 51.28 | 0.83 |
| Average | 63.49 | 41.63 | 0.65 |
| S.D. | 8.42 | 9.43 | 0.11 |
| COV (%) | 13.26 | 22.65 | 16.60 |

TABLE 19

ISR Data for Fibers Relaxed with Fiber Elasticity Conserving Sodium Hydroxide Relaxer 5C

| Fiber No. | ISR Value Before Relaxer 5C | ISR Value After Relaxer 5C | Calculated ISR Index |
| --- | --- | --- | --- |
| 1 | 68.53 | 24.21 | 0.35 |
| 2 | 58.32 | 34.56 | 0.59 |
| 3 | 57.73 | 28.27 | 0.49 |
| 4 | 49.09 | 23.84 | 0.49 |
| 5 | 50.49 | 14.43 | 0.29 |
| 6 | 62.18 | 31.09 | 0.50 |
| 7 | 62.93 | 21.72 | 0.34 |
| 8 | 66.95 | 32.65 | 0.49 |
| 9 | 62.15 | 33.16 | 0.53 |
| 10 | 54.10 | 12.62 | 0.23 |
| 11 | 76.19 | 47.97 | 0.63 |
| 12 | 57.65 | 16.39 | 0.28 |
| 13 | 74.61 | 26.82 | 0.36 |
| 14 | 68.04 | 19.83 | 0.29 |
| 15 | 64.06 | 39.05 | 0.61 |
| Average | 62.20 | 27.11 | 0.43 |
| S.D. | 7.93 | 9.65 | 0.13 |
| COV (%) | 12.75 | 35.61 | 30.44 |

Based on the calculated average ISR indices, the % loss of wet fiber elasticity was about 29% from Relaxer 5A with no discernible amelioration from Relaxers 5B and 5C. A statistical analysis of the average ISR Index using ANOVA Tukey B Test found no significant difference between the average ISR Index of Relaxers 5A, 5B, and 5C. However, when the average ISR Index of 13 fibers relaxed with Relaxer 5A (ISR Index 0.71) was compared by independent T-test to that of the average ISR Index of the 12 fibers relaxed with the comparative sodium hydroxide Relaxer of Example 4 (0.63), the average increased ISR index of the hair relaxed with Relaxer 5A (0.97% PPDM) was judged statistically higher than that of the comparative Relaxer 4A at p=0.025. Thus, surprisingly, the presence of about 0.97% high viscosity PPDM in the relaxer was judged as conserving hair fiber elasticity by reducing the loss of wet fiber elasticity to less than 30% relative to the 33% loss from that of the comparative Relaxer 4A.

Example 6. Fiber Elasticity Conserving Alkali Metal Hydroxide Relaxer

This example illustrates the amelioration in loss of fiber elasticity from an alkalki metal hydroxide (lye-type) hair relaxer containing sodium hydroxide at an active concentration in the range of about 2 to 2.5 weight % when the fiber-elasticity conserving agent propoxytetramethyl piperidinyl dimethicone (PPDM) is present.

Lye-type, sodium hydroxide relaxers were prepared containing, as the fiber elasticity conserving agent, MICROSIL HAF-HV sub-micron emulsion, present in the hair relaxer, at a concentration, as supplied, of about 3.2% (Relaxer 6A); of about 7% (Relaxer 6B); and of about 10.7% (Relaxer 6C). MICROSIL HAF-HV is the tradename for the high viscosity material having the INCI name: Propoxytetramethyl Piperidinyl Dimethicone (and) C11-15 Pareth-7 (and) Trideceth-6, and was supplied as an aqueous, submicron emulsion of 30% propoxytetramethyl piperidinyl dimethicone, (DIMETHISIL HNH-HV). Thus the active concentration of the fiber elasticity conserving agent, propoxytetramethyl piperidinyl dimethicone (PPDM), used in Relaxer 6A was about 0.97%; in Relaxer 6B was about 2.1%; and in Relaxer 6C was about 3.21%.

The compositions of hair Relaxers 6A, 6B, and 6C are shown in Table 20. The relaxer creams were prepared as described in Example 4, except that after the oil phase and water phase were mixed together to form the emulsion, the emulsion was cooled to a temperature of about 55° C. and the fiber elasticity agent (ingredient 9) was added and mixed for about 5 minutes before proceeding with the cooling step and addition of the sodium hydroxide.

The general Hair Relaxer/ISR procedure described in section I-A was followed using each one of hair Relaxers 6A, 6B and 6C. The ISR values of 12 selected fiber determined before and after the individual Relaxer treatment and the calculated ISR Index obtained with hair Relaxer 6A are shown in Table 21; with hair Relaxer 6B are shown in Table 22 and with hair Relaxer 6C are shown in Table 23.

TABLE 20

Fiber Elasticity Conserving Sodium Hydroxide Hair Relaxer with Propoxytetramethyl piperidinyl dimethicone (PPDM)

| Ingredient (Common/Tradename/INCI Name) | % Weight (As supplied) Relaxer 6A | % Weight (As supplied) Relaxer 6B | % Weight (As supplied) Relaxer 6C |
|---|---|---|---|
| 1. Petrolatum | 23 | 23 | 23 |
| 2. Mineral oil | 13.5 | 13.5 | 13.5 |
| 3. Emulsifying wax N.F. | 11 | 11 | 11 |
| 4. LANETH-15 | 1 | 1 | 1 |
| 5. PEG-75-LANOLIN | 0.5 | 0.5 | 0.5 |
| 6. Water to 100% | q.s. | q.s. | q.s. |
| 7. Propylene glycol | 2 | 2 | 2 |
| 8. Sodium hydroxide | 2.2 | 2.2 | 2.2 |
| 9. MICROSIL HAF-HV (30% PPDM) | 3.2 | 7 | 10.7 |

TABLE 21

ISR Data for Fibers Relaxed with Fiber Elasticity Conserving Sodium Hydroxide Relaxer 6A

| Fiber No. | ISR Value Before Relaxer 6A | ISR Value After Relaxer 6A | Calculated ISR Index |
|---|---|---|---|
| 1 | 57.78 | 37.05 | 0.64 |
| 2 | 62.13 | 28.84 | 0.46 |
| 3 | 46.72 | 23.58 | 0.50 |
| 4 | 54.63 | 32.27 | 0.59 |
| 5 | 55.71 | 34.59 | 0.62 |
| 6 | 70.25 | 46.42 | 0.66 |
| 7 | 49.40 | 32.99 | 0.67 |
| 8 | 58.53 | 32.21 | 0.55 |
| 9 | 66.12 | 42.16 | 0.64 |
| 10 | 66.74 | 41.37 | 0.62 |
| 11 | 31.10 | 27.02 | 0.87 |
| 12 | 59.73 | 34.24 | 0.57 |
| Average | 56.57 | 34.39 | 0.62 |
| S.D. | 10.57 | 6.57 | 0.10 |
| COV (%) | 18.69 | 19.09 | 16.43 |

TABLE 22

ISR Data for Fibers Relaxed with Fiber Elasticity Conserving Sodium Hydroxide Relaxer 6B

| Fiber No. | ISR Value Before Relaxer 6B | ISR Value After Relaxer 6B | Calculated ISR Index |
|---|---|---|---|
| 1 | 53.09 | 38.47 | 0.72 |
| 2 | 54.86 | 38.77 | 0.71 |
| 3 | 61.32 | 43.44 | 0.71 |
| 4 | 63.50 | 34.65 | 0.55 |
| 5 | 65.53 | 43.75 | 0.67 |
| 6 | 61.92 | 34.01 | 0.55 |
| 7 | 61.71 | 48.44 | 0.79 |
| 8 | 55.87 | 37.12 | 0.66 |
| 9 | 70.22 | 36.61 | 0.52 |
| 10 | 63.16 | 41.94 | 0.66 |
| 11 | 65.79 | 47.69 | 0.73 |
| 12 | 68.00 | 40.30 | 0.59 |
| Average | 62.08 | 40.43 | 0.66 |
| S.D. | 5.244 | 4.730 | 0.084 |
| COV (%) | 8.45 | 11.70 | 12.83 |

TABLE 23

ISR Data for Fibers Relaxed with Fiber Elasticity Conserving Sodium Hydroxide Relaxer 6C

| Fiber No. | ISR Value Before Relaxer 6C | ISR Value After Relaxer 6C | Calculated ISR Index |
|---|---|---|---|
| 1 | 43.19 | 38.84 | 0.90 |
| 2 | 54.48 | 34.49 | 0.63 |
| 3 | 51.63 | 36.45 | 0.71 |
| 4 | 44.39 | 39.73 | 0.89 |
| 5 | 47.95 | 37.18 | 0.78 |
| 6 | 44.49 | 40.52 | 0.91 |
| 7 | 46.20 | 36.09 | 0.78 |
| 8 | 70.26 | 50.47 | 0.72 |
| 9 | 65.85 | 45.62 | 0.69 |
| 10 | 68.40 | 55.75 | 0.82 |
| 11 | 69.99 | 36.59 | 0.52 |
| 12 | 60.33 | 41.65 | 0.69 |
| Average | 55.60 | 41.12 | 0.75 |
| S.D. | 10.79 | 6.44 | 0.12 |
| COV (%) | 19.41 | 15.67 | 15.49 |

Based on the calculated average ISR indices, the % loss of wet fiber elasticity was about 38% from Relaxer 6A, about 34% from Relaxer 6B, and about 25% from Relaxer 6C. A statistical analysis of the average ISR Index using a one-way ANOVA Tukey test found a significant difference between the average ISR Index (0.75) of Relaxer 6C compared to that of the average ISR Index of fibers relaxed with the comparative sodium hydroxide Relaxer 4A of example 4 (0.63). The increased average ISR index of the hair relaxed with Relaxer 6C was judged statistically higher than that of the comparative Relaxer 4A at p<0.05. Thus, surprisingly, the presence of about 3.2% high-viscosity PPDM in an emulsion form in the relaxer was judged to conserve hair fiber elasticity by reducing loss of wet fiber elasticity to less than 30% relative to that of the comparative Relaxer 4A.

Example 7. Fiber Elasticity Conserving Guanidine Hydroxide Relaxer

This example illustrates the amelioration in loss of hair fiber elasticity during hair relaxation with a no-lye type, guanidine hydroxide relaxer when a hair fiber elasticity conserving agent, proproxytetramethyl piperidinyl dimethicone was present. Three different concentrations of fiber elasticity conserving agent were evaluated and wet fiber elasticity was measured by the ISR Method I as described above.

No-lye type, guanidine hydroxide relaxers were prepared containing, as the fiber elasticity conserving agent, medium viscosity DIMETHISIL HNH-MV, at a concentration, as supplied, of about 0.97% (Relaxer 7A); of about 2.1% (Relaxer 7B); and of about 3.2% (Relaxer 7C). The composition of Relaxers 7A, 7B, and 7C are shown in Table 24. DIMETHISIL HNH-MV is the tradename for INCI: Propoxytetramethyl Piperidinyl Dimethicone as described above in the Materials section.

TABLE 24

Guanidine Hydroxide Relaxer with Fiber Elasticity Conserving Agent Propoxytetramethyl Piperidinyl Dimethicone (PPDM)

| Component | Relaxer 7A Wt. % | Relaxer 7B Wt. % | Relaxer 7C Wt. % |
| --- | --- | --- | --- |
| Part A: Relaxer Cream Base of Table 1 | 78.13 | 77 | 75.9 |
| Part B: Liquid Activator of Table 2 | 20.9 | 20.9 | 20.9 |
| Part C: DIMETHISIL HNH-MV | 0.97 | 2.1 | 3.2 |

The guanidine hydroxide relaxers, 7A, 7B, and 7C, were prepared by mixing together the components shown in Table 24 substantially immediately before using on the hair. The hair relaxer procedure of Example 1 was followed except that a first set of hair fibers was relaxed with Relaxer 7A; a separate second set was relaxed with Relaxer 7B and a separate third set was relaxed with Relaxer 7C of Table 24.

The ISR Data for the fibers relaxed with the composition of Example 7A is shown in Table 25, with the composition of Example 7B is shown in Table 26; and with the composition of Example 7C is shown in Table 27.

TABLE 25

ISR Data for Fibers Relaxed With Fiber Elasticity Conserving Guanidine Hydroxide Relaxer 7A

| Fiber No. | ISR Value Before Relaxer 7A | ISR Value After Relaxer 7A | Calculated ISR Index |
| --- | --- | --- | --- |
| 1 | 63.42 | 54.25 | 0.86 |
| 2 | 57.53 | 34.41 | 0.60 |
| 3 | 68.59 | 62.11 | 0.91 |
| 4 | 56.82 | 49.27 | 0.87 |
| 5 | 34.62 | 23.12 | 0.67 |
| 6 | 44.77 | 35.68 | 0.80 |
| 7 | 51.38 | 45.11 | 0.88 |
| 8 | 54.07 | 41.16 | 0.76 |
| 9 | 52.34 | 48.61 | 0.93 |
| 10 | 39.85 | 25.94 | 0.65 |
| 11 | 48.12 | 44.73 | 0.93 |
| 12 | 74.49 | 59.34 | 0.80 |
| Average | 53.84 | 43.64 | 0.80 |
| S.D. | 10.98 | 11.72 | 0.11 |
| COV (%) | 20.39 | 26.86 | 13.44 |

TABLE 26

ISR Data for Fibers Relaxed With Fiber Elasticity Conserving Guanidine Hydroxide Relaxer 7B

| Fiber No. | ISR Value Before Relaxer 7B | ISR Value After Relaxer 7B | Calculated ISR Index |
| --- | --- | --- | --- |
| 1 | 59.10 | 42.29 | 0.72 |
| 2 | 65.19 | 47.52 | 0.73 |
| 3 | 48.95 | 24.51 | 0.50 |
| 4 | 49.96 | 45.52 | 0.91 |
| 5 | 47.35 | 18.97 | 0.40 |
| 6 | 59.83 | 49.64 | 0.83 |
| 7 | 40.58 | 25.51 | 0.63 |
| 8 | 67.47 | 47.62 | 0.71 |
| 9 | 61.10 | 32.65 | 0.53 |
| 10 | 60.91 | 35.67 | 0.59 |
| 11 | 44.63 | 39.66 | 0.89 |
| 12 | 54.94 | 40.53 | 0.74 |
| Average | 55.00 | 37.51 | 0.68 |
| S.D. | 8.57 | 10.15 | 0.16 |
| COV (%) | 15.58 | 27.07 | 23.04 |

TABLE 27

ISR Data for Fibers Relaxed With Fiber Elasticity Conserving Guanidine Hydroxide Relaxer 7C

| Fiber No. | ISR Value Before Relaxer 7C | ISR Value After Relaxer 7C | Calculated ISR Index |
| --- | --- | --- | --- |
| 1 | 46.36 | 29.18 | 0.63 |
| 2 | 58.07 | 32.41 | 0.56 |
| 3 | 57.66 | 31.71 | 0.55 |
| 4 | 46.39 | 18.35 | 0.40 |
| 5 | 59.44 | 36.78 | 0.62 |
| 6 | 65.46 | 38.26 | 0.58 |
| 7 | 55.84 | 23.29 | 0.42 |
| 8 | 68.18 | 42.13 | 0.62 |
| 9 | 58.13 | 38.09 | 0.66 |
| 10 | 61.77 | 42.29 | 0.68 |
| 11 | 57.64 | 42.01 | 0.73 |
| 12 | 51.99 | 38.73 | 0.75 |
| Average | 57.25 | 34.44 | 0.60 |
| S.D. | 6.61 | 7.7 | 0.11 |
| COV (%) | 11.54 | 22.36 | 18.10 |

A statistical analysis of the data using ANOVA Tukey B test showed that Relaxer 7A>7B>7C in conserving fiber elasticity of the hair. Based on the calculated average ISR indices, the fibers relaxed with any one of the Relaxers 7A, 7B and 7C were judged statistically significantly stronger than the fibers relaxed with the comparative Relaxer 1A of Example 1 at p<0.05. Thus, relative to the comparative Relaxer 1A, the presence of medium-viscosity PPDM reduced the % loss of wet fiber elasticity from 60% to about 20% from Relaxer 7A, to about 32% from Relaxer 7B, and to about 40% from Relaxer 7C.

Example 8. Fiber Elasticity Conserving Guanidine Hydroxide Relaxer

This example illustrates the amelioration in loss of hair fiber elasticity during hair relaxation with a no-lye type, guanidine hydroxide relaxer when a hair fiber elasticity conserving agent, proproxytetramethyl piperidinyl dimethicone was present. Two different concentrations of the fiber elasticity conserving agent were evaluated and wet fiber elasticity was measured by the ISR Method I as described above.

Two no-lye type, guanidine hydroxide relaxers were prepared containing, as the fiber elasticity conserving agent, MICROSIL HAF-MV sub-micron emulsion, present in the hair relaxer at a concentration, as supplied, of about 3.2% (Relaxer 8A); of about 10.7% (Relaxer 8B) as shown in Table 28. As described above, MICROSIL HAF-MV is the tradename for the material having the INCI name: Propoxytetramethyl Piperidinyl Dimethicone (and) C11-15 Pareth-7 (and) Trideceth-6, and was supplied as an aqueous, submicron emulsion comprising 30% propoxytetramethyl piperidinyl dimethicone, (DIMETHISIL HNH-MV). Thus the active concentration of the fiber elasticity conserving agent, propoxytetramethyl piperidinyl dimethicone (PPDM), used in Relaxer 8A was about 0.97%, and in Relaxer 8B was about 3.21%.

TABLE 28

Guanidine Hydroxide Relaxer with Fiber Elasticity Conserving Agent Propoxytetramethyl Piperidinyl Dimethicone (PPDM)

| Component | Relaxer 8A Wt. % | Relaxer 8B Wt. % |
|---|---|---|
| Part A: Relaxer Cream Base of Table 1 | 75.9 | 68.4 |
| Part B: Liquid Activator of Table 2 | 20.9 | 20.9 |
| Part C: MICROSIL HAF-MV (30% PPDM) | 3.2 | 10.7 |

The guanidine hydroxide relaxers, 8A, and 8B were prepared by mixing together the components shown in Table 28 substantially immediately before using on the hair. The hair relaxer procedure of Example 1 was followed except that a first set of hair fibers was relaxed with Relaxer 8A; and a separate second set was relaxed with Relaxer 8B of Table 28.

The ISR Data for 12 fibers relaxed with the composition of Example 8A is shown in Table 29, and 12 for fibers relaxed with the composition of Example 8B shown in Table 30.

TABLE 29

ISR Data of Fibers Relaxed with Fiber Elasticity Conserving Guanidine Hydroxide Relaxer 8A

| Fiber No. | ISR Value Before Relaxer 8A | ISR Value After Relaxer 8A | Calculated ISR Index |
|---|---|---|---|
| 1 | 65.7 | 27.8 | 0.42 |
| 2 | 68.8 | 38.5 | 0.56 |
| 3 | 62.4 | 47.0 | 0.75 |
| 4 | 43.9 | 26.1 | 0.59 |
| 5 | 69.2 | 48.0 | 0.69 |

TABLE 29-continued

ISR Data of Fibers Relaxed with Fiber Elasticity Conserving Guanidine Hydroxide Relaxer 8A

| Fiber No. | ISR Value Before Relaxer 8A | ISR Value After Relaxer 8A | Calculated ISR Index |
|---|---|---|---|
| 6 | 71.5 | 46.9 | 0.66 |
| 7 | 58.6 | 42.1 | 0.72 |
| 8 | 55.4 | 36.8 | 0.66 |
| 9 | 55.1 | 40.2 | 0.73 |
| 10 | 59.7 | 46.2 | 0.77 |
| 11 | 55.4 | 36.5 | 0.66 |
| 12 | 69.7 | 48.5 | 0.70 |
| Average | 61.3 | 40.4 | 0.66 |
| S.D. | 8.17 | 7.63 | 0.10 |
| COV (%) | 13.33 | 18.90 | 14.68 |

TABLE 30

ISR of Fibers Relaxed with Fiber Elasticity Guanidine Hydroxide Relaxer 8B

| Fiber No. | ISR Value Before Relaxer 8B | ISR Value After Relaxer 8B | Calculated ISR Index |
|---|---|---|---|
| 1 | 71.12 | 61.14 | 0.86 |
| 2 | 59.78 | 55.58 | 0.93 |
| 3 | 68.91 | 48.57 | 0.71 |
| 4 | 70.51 | 50.52 | 0.72 |
| 5 | 56.07 | 27.89 | 0.50 |
| 6 | 60.46 | 47.16 | 0.78 |
| 7 | 52.23 | 41.72 | 0.80 |
| 8 | 78.65 | 69.42 | 0.88 |
| 9 | 69.22 | 66.53 | 0.96 |
| 10 | 70.55 | 59.63 | 0.85 |
| 11 | 68.31 | 31.57 | 0.46 |
| 12 | 53.65 | 48.43 | 0.90 |
| Average | 64.95 | 50.68 | 0.78 |
| S.D | 8.25 | 12.80 | 0.16 |
| COV (%) | 12.70 | 25.26 | 20.60 |

The statistical analysis of the data by ANOVA Tukey B Test compared to that of the comparative Relaxer 1A of Example 1 (ISR Index 0.4) showed that, on average, the fiber elasticity of hair relaxed with either Relaxer 8A (ISR Index 0.66) or Relaxer 8B (ISR Index 0.78) was significantly stronger than that of comparative Relaxer 1A at p=<0.05. The amelioration in loss of fiber elasticity obtained with Relaxer 8B was judged greater than that obtained with Relaxer 8A. Relative to the comparative Relaxer 1A, the presence of the medium viscosity emulsion form PPDM in Relaxer 8A and 8B reduced the loss in wet hair fiber elasticity from 60% to about 34% to about 22%, respectively, based on the calculated average ISR indices.

Example 9. Fiber Elasticity Conserving Alkali Metal Hydroxide Relaxer

This example illustrates the amelioration in loss of fiber elasticity from an alkali metal hydroxide, (lye-type), hair relaxer containing sodium hydroxide at an active concentration in the range of about 2 to 2.5 weight % when the fiber-elasticity conserving agent propoxytetramethyl piperidinyl dimethicone is present.

Lye-type, sodium hydroxide relaxers were prepared containing, as the fiber elasticity conserving agent, medium viscosity DIMETHISIL HNH-MV at a concentration, as supplied, of about 0.97% (Relaxer 9A); of about 2.1% (Relaxer 9B); and of about 3.2% (Relaxer 9C). The compositions of hair Relaxers 9A, 9B, and 9C are shown in Table 31. The relaxer creams were prepared as described in Example 4, except that after the oil phase and water phase were mixed together to form the emulsion, the emulsion was cooled to a temperature of about 55° C. and the fiber elasticity agent (ingredient 9) was added and mixed for about 5 minutes before proceeding with the cooling step and addition of the sodium hydroxide.

The general Hair Relaxer/ISR procedure described in section I-A was followed using each one of hair Relaxers 9A, 9B and 9C. The ISR values of 12 selected fiber were determined before and after the individual Relaxer treatments with Relaxers 9A and 9B and the ISR value of 10 selected fibers were determined before and after Relaxer treatment with Relaxer 9C. The calculated ISR values and calculated ISR Index obtained with hair Relaxer 9A are shown in Table 32; with hair Relaxer 9B are shown in Table 33 and with hair Relaxer 9C are shown in Table 34.

TABLE 31

Fiber Conserving Sodium Hydroxide Hair Relaxer with Propoxytetramethyl Piperidinyl Dimethicone (PPDM)

| Ingredient (Common/Tradename/ INCI Name) | % Weight (As supplied) Relaxer 9A | % Weight (As supplied) Relaxer 9B | % Weight (As supplied) Relaxer 9C |
|---|---|---|---|
| 1. Petrolatum | 23 | 23 | 23 |
| 2. Mineral oil | 13.5 | 13.5 | 13.5 |
| 3. Emulsifying wax N.F. | 11 | 11 | 11 |
| 4. LANETH-15 | 1 | 1 | 1 |
| 5. PEG-75-LANOLIN | 0.5 | 0.5 | 0.5 |
| 6. Water to 100% | q.s. | q.s. | q.s. |
| 7. Propylene glycol | 2 | 2 | 2 |
| 8. Sodium hydroxide | 2.2 | 2.2 | 2.2 |
| 9. DIMETHISIL HNH-MV | 0.97 | 2.1 | 3.2 |

TABLE 32

ISR Data for Fibers Relaxed with Fiber Elasticity Conserving Sodium Hydroxide Relaxer 9A

| Fiber No. | ISR Value Before Relaxer 9A | ISR Value After Relaxer 9A | Calculated ISR Index |
|---|---|---|---|
| 1 | 57.87 | 42.79 | 0.74 |
| 2 | 66.95 | 49.98 | 0.75 |
| 3 | 53.51 | 34.78 | 0.65 |
| 4 | 73.05 | 48.93 | 0.67 |
| 5 | 83.63 | 69.18 | 0.83 |
| 6 | 54.02 | 42.88 | 0.79 |
| 7 | 58.87 | 46.70 | 0.79 |
| 8 | 59.85 | 36.60 | 0.61 |
| 9 | 62.05 | 36.73 | 0.59 |
| 10 | 38.25 | 28.26 | 0.74 |
| 11 | 67.32 | 44.66 | 0.66 |
| 12 | 67.40 | 52.49 | 0.78 |
| Average | 61.90 | 44.50 | 0.72 |
| S.D. | 11.29 | 10.51 | 0.08 |
| COV (%) | 18.25 | 23.61 | 10.80 |

TABLE 33

ISR Data for Fibers Relaxed with Fiber Elasticity Conserving Sodium Hydroxide Relaxer 9B

| Fiber No. | ISR Value Before Relaxer 9B | ISR Value After Relaxer 9B | Calculated ISR Index |
|---|---|---|---|
| 1 | 70.43 | 50.78 | 0.72 |
| 2 | 68.08 | 41.32 | 0.61 |
| 3 | 54.19 | 42.10 | 0.78 |
| 4 | 65.54 | 40.87 | 0.62 |
| 5 | 66.56 | 26.87 | 0.40 |
| 6 | 68.31 | 38.72 | 0.57 |
| 7 | 72.86 | 51.00 | 0.70 |
| 8 | 53.85 | 25.39 | 0.47 |
| 9 | 59.40 | 30.57 | 0.51 |
| 10 | 60.80 | 47.12 | 0.78 |
| 11 | 52.34 | 29.03 | 0.55 |
| 12 | 49.21 | 26.85 | 0.55 |
| Average | 61.80 | 37.55 | 0.61 |
| S.D. | 7.93 | 9.50 | 0.12 |
| COV (%) | 12.83 | 25.30 | 19.64 |

TABLE 34

ISR Data for Fibers Relaxed with Fiber Elasticity Conserving Sodium Hydroxide Relaxer 9C

| Fiber No. | ISR Value Before Relaxer 9C | ISR Value After Relaxer 9C | Calculated ISR Index |
|---|---|---|---|
| 1 | 62.79 | 42.43 | 0.68 |
| 2 | 62.97 | 43.92 | 0.70 |
| 3 | 65.83 | 26.35 | 0.40 |
| 4 | 66.20 | 52.74 | 0.80 |
| 5 | 58.32 | 33.02 | 0.57 |
| 6 | 68.04 | 54.59 | 0.80 |
| 7 | 58.54 | 38.76 | 0.66 |
| 8 | 60.64 | 38.88 | 0.64 |
| 9 | 63.84 | 26.24 | 0.41 |
| 10 | 53.62 | 33.97 | 0.63 |
| Average | 62.08 | 39.09 | 0.63 |
| S.D. | 4.36 | 9.73 | 0.14 |
| COV (%) | 7.03 | 24.89 | 21.88 |

A statistical analysis by Independent T-Test, showed that, on average, the increased wet fiber elasticity (ISR Index: 0.72) achieved with Relaxer 9A was judged significantly stronger than the wet fiber elasticity (ISR Index: 0.63) of the comparative Relaxer 4A of Example 4 at p=0.03. Relative to the comparative Relaxer 4A, the presence of about 0.97% medium viscosity PPDM in Relaxer 9A reduced the loss of wet fiber elasticity from 37% to about 28%, based on the calculated average ISR indices.

Example 10. Fiber Elasticity Conserving Alkali Metal Hydroxide Relaxer

This example illustrates the amelioration in loss of hair fiber elasticity during hair relaxation with an alkali metal hydroxide, (lye type), hair relaxer 10A containing sodium hydroxide when a hair fiber elasticity conserving agent, proproxytetramethyl piperidinyl dimethicone (PPDM) was present at an active concentration of about 3.2%. Fiber elasticity was measured by the ISR Method I as described above.

Lye type sodium hydroxide relaxer 10A was prepared following the procedure of Example 4, except that the fiber elasticity conserving agent was MICROSIL HAF-MV submicron emulsion, present in the hair relaxer at a concentration, as supplied, of about 10.7% (Relaxer 10A). As described above, MICROSIL HAF-MV is the tradename for the material having the INCI name: Propoxytetramethyl Piperidinyl Dimethicone (and) C11-15 Pareth-7 (and) Trideceth-6, and was supplied as an aqueous, submicron emulsion comprising 30% propoxy-tetramethyl piperidinyl dimethicone, (DIMETHISIL HNH-MV). Thus the active concentration of the fiber elasticity conserving agent, propoxytetramethyl piperidinyl dimethicone (PPDM), used in Relaxer 10A was about 3.2% as shown in Table 35.

The general Hair Relaxer/ISR procedure described in section I-A was followed using each hair Relaxer 10A. The ISR values of 12 selected fiber determined before and after the individual Relaxer treatment and the calculated ISR Index obtained with hair Relaxer 10A are shown in Table 36.

TABLE 35

Fiber Elasticity Conserving Sodium Hydroxide Hair Relaxer 10A with Propoxytetramethyl piperidinyl dimethicone (PPDM)

| Ingredient (Common/Trade/INCI Name) | % Weight (As supplied) Relaxer 10A |
|---|---|
| 1. Petrolatum | 23 |
| 2. Mineral oil | 13.5 |
| 3. Emulsifying wax N.F. | 11 |
| 4. LANETH-15 | 1 |
| 5. PEG-75-LANOLIN | 0.5 |
| 6. Water to 100% | q.s. |
| 7. Propylene glycol | 2 |
| 8. Sodium hydroxide | 2.2 |
| 9. MICROSIL HAF-HV (30% PPDM) | 10.7 |

TABLE 36

ISR Data for Fibers Relaxed with Fiber Elasticity Sodium Hydroxide Relaxer 10A

| Fiber No. | ISR Value Before Relaxer 10A | ISR Value After Relaxer 10A | Calculated ISR Index |
|---|---|---|---|
| 1 | 90.93 | 76.27 | 0.84 |
| 2 | 59.74 | 50.46 | 0.84 |
| 3 | 66.68 | 46.06 | 0.69 |
| 4 | 59.06 | 46.72 | 0.79 |
| 5 | 60.31 | 48.43 | 0.80 |
| 6 | 70.20 | 58.77 | 0.84 |
| 7 | 56.30 | 51.03 | 0.91 |
| 8 | 49.04 | 43.24 | 0.88 |
| 9 | 72.63 | 65.77 | 0.91 |
| 10 | 62.58 | 53.68 | 0.86 |
| 11 | 49.50 | 36.39 | 0.74 |
| 12 | 53.65 | 46.01 | 0.86 |
| Average | 62.55 | 51.90 | 0.83 |
| S.D. | 11.60 | 10.71 | 0.07 |
| COV (%) | 18.54 | 20.64 | 7.86 |

A statistical analysis was conducted using Independent T Test and indicated that, on average, the fiber elasticity achieved with Relaxer 10A (ISR Index: 0.83) was significantly greater than that of the fiber elasticity (ISR Index: 0.63) of comparative sodium hydroxide Relaxer 4A of Example 4 at p=0.00. Relative to the comparative Relaxer 4A, the presence of about 3.2%, medium viscosity PPDM in emulsion form in Relaxer 10A reduced the loss of wet fiber elasticity from 37% to about 17%.

Example 11. Fiber Elasticity Conserving Guanidine Hydroxide Relaxer

This example illustrates the amelioration in loss of hair fiber elasticity during hair relaxation with a no-lye type, guanidine hydroxide relaxer when a hair fiber elasticity conserving agent, proproxytetramethyl piperidinyl dimethicone was present. A no-lye type, guanidine hydroxide relaxer Relaxer 11A was prepared containing, as the fiber elasticity conserving agent, low viscosity PPDM, DIMETHISIL HNH-LV, at a concentration, as supplied, of about 0.97%. The composition of Relaxer 11A is shown in Table 37.

TABLE 37

Fiber Elasticity Conserving Guanidine Hydroxide Relaxer 11A

| Component | Relaxer 11A Wt. % |
|---|---|
| Part A: Relaxer Cream Base of Table 1 | 78.13 |
| Part B: Liquid Activator of Table 2 | 20.9 |
| Part C: DIMETHISIL HNH-LV | 0.97 |
| pH = 13.1 | |

The guanidine hydroxide Relaxer 11A was prepared by mixing together the components shown in Table 37 substantially immediately before using on the hair. The hair relaxer procedure of Example 1 was followed except that the hair fibers were relaxed with Relaxer 11A. The wet fiber elasticity of 12 selected fibers was determined before and after relaxation measured by the ISR Method I as described above and the data are shown in Table 38.

TABLE 38

ISR Data for Fibers Relaxed with Fiber Elasticity Conserving Guanidine Hydroxide Relaxer 11A

| Fiber No. | ISR Value Before Relaxer 11A | ISR Value After Relaxer 11A | Calculated ISR Index |
|---|---|---|---|
| 1 | 57.41 | 43.45 | 0.76 |
| 2 | 60.33 | 43.57 | 0.72 |
| 3 | 54.93 | 46.01 | 0.84 |
| 4 | 48.08 | 37.11 | 0.78 |
| 5 | 55.48 | 40.16 | 0.72 |
| 6 | 65.99 | 58.57 | 0.89 |
| 7 | 60.19 | 48.55 | 0.81 |
| 8 | 61.29 | 50.46 | 0.82 |
| 9 | 73.28 | 55.48 | 0.76 |
| 10 | 67.25 | 39.07 | 0.58 |
| 11 | 70.43 | 55.22 | 0.78 |
| 12 | 53.05 | 37.83 | 0.71 |
| Average | 60.64 | 46.29 | 0.76 |
| S.D. | 7.47 | 7.38 | 0.08 |
| COV (%) | 12.31 | 15.94 | 10.14 |

A statistical comparison of the average fiber elasticity (ISR Index: 0.76) of tresses relaxed with Relaxer 11A relative to that of the comparative guanidine hydroxide Relaxer 1A of Example 1 (ISR Index: 0.40) showed that, on average, the fiber elasticity achieved with Relaxer 11A was significantly higher at p=0.000. Relative to the comparative Relaxer 1A, the presence of about 0.97% low viscosity PPDM in Relaxer 11A reduced the loss of wet fiber elasticity from 60% to about 24%, based on the calculated average ISR indices.

Example 12. Fiber Elasticity Conserving Alkali Metal Hydroxide Relaxer

This example illustrates the amelioration in loss of hair fiber elasticity during hair relaxation with an alkali metal hydroxide, (lye-type) relaxer having about 2 to 2.5% sodium hydroxide when a hair fiber elasticity conserving agent, proproxytetramethyl piperidinyl dimethicone was present. Lye-type, sodium hydroxide Relaxer 12A was prepared containing, as the filter elasticity conserving agent, low viscosity PPDM, DIMETHISIL HNH-LV, at a concentration, as supplied, of about 0.97% (Relaxer 12A). The composition of Relaxer 12A is shown in Table 39.

TABLE 39

Fiber Elasticity Conserving Sodium Hydroxide Relaxer 12A with Propoxytetramethyl (piperidinyl) dimethicone (PPDM)

| Ingredient (Common/Trade/INCI Name) | % Weight (As supplied) Relaxer 12A |
|---|---|
| 1. Petrolatum | 23 |
| 2. Mineral oil | 13.5 |
| 3. Emulsifying wax N.F. | 11 |
| 4. LANETH-15 | 1 |
| 5. PEG-75-LANOLIN | 0.5 |
| 6. Water to 100% | q.s. |
| 7. Propylene glycol | 2 |
| 8. Sodium hydroxide | 2.2 |
| 9. DIMETHISIL HNH-LV pH = 14.1 | 0.97 |

The sodium hydroxide Relaxer 12A was prepared generally following the procedure of Example 4, except that after the oil phase and water phase were mixed together to form the emulsion, the emulsion was cooled to a temperature of about 55° C. and the fiber elasticity agent (ingredient 9) was added and mixed for about 5 minutes before proceeding with the further cooling step and addition of the sodium hydroxide. The ISR/relaxer procedure of Example 1 was followed and the fiber elasticity of the tresses before and after Relaxer 12A was determined and the average ISR Index was calculated. The fiber elasticity data are shown in Table 40.

TABLE 40

ISR Data for Fibers Relaxed with Fiber Elasticity Conserving Sodium Hydroxide Relaxer 12A

| Fiber No. | ISR Value Before Relaxer 12A | ISR Value After Relaxer 12A | Calculated ISR Index |
|---|---|---|---|
| 1 | 53.99 | 32.13 | 0.59 |
| 2 | 70.36 | 60.50 | 0.86 |
| 3 | 61.78 | 45.77 | 0.74 |
| 4 | 62.70 | 47.76 | 0.76 |
| 5 | 65.96 | 36.07 | 0.55 |
| 6 | 52.65 | 42.81 | 0.81 |
| 7 | 73.85 | 57.54 | 0.78 |
| 8 | 58.51 | 32.22 | 0.55 |
| 9 | 57.01 | 43.92 | 0.77 |
| 10 | 57.37 | 38.01 | 0.66 |
| 11 | 57.77 | 43.23 | 0.75 |
| 12 | 36.45 | 26.78 | 0.73 |
| Average | 59.03 | 42.23 | 0.71 |
| S.D. | 9.14 | 9.63 | 0.10 |
| COV (%) | 15.48 | 22.80 | 13.72 |

Relative to the comparative Relaxer 4A of Example 4, the presence of about 0.97% low viscosity of PPDM in Relaxer 12A reduced the loss of wet fiber elasticity from 37% to about 29%, based on the calculated average ISR indices. Thus, the increased wet fiber elasticity achieved with Relaxer 12A, on average, (ISR Index: 0.71) was about 13% higher than the fiber elasticity, (ISR Index: 0.63), of the comparative Relaxer 4A of Example 4, though a data comparison analysis by Independent T-Test did not show this to be a significant increase.

Example 13. Fiber Elasticity Conserving Guanidine Hydroxide Relaxer

This example illustrates the amelioration in loss of wet hair fiber elasticity during hair relaxation with a no-lye type, guanidine hydroxide Relaxer when a combination of a hair fiber elasticity conserving agent, proproxytetramethyl piperidinyl dimethicone (PPDM), and at least one quaternary ammonium compound was present.

A no-lye type, guanidine hydroxide Relaxer 13A was prepared containing MICROSIL VOLUME at a concentration, as supplied, of about 3.9% as shown in Table 42. As described in the Materials section, MICROSIL VOLUME is the tradename for the material having the INCI name: Propoxytetramethyl Piperidinyl Dimethicone (and) Cetrimonium Chloride (and) C11-C15 Pareth-7 (and) Trideceth-6. MICROSIL VOLUME was supplied as an aqueous, o/w submicron emulsion comprising about 20% medium viscosity Propoxytetramethyl Piperidinyl Dimethicone (DIMETHISIL-MV) and about 5% Cetrimonium Chloride. Thus, the concentration used, as supplied, provided about 0.8% active PPDM and about 0.2% quaternary ammonium compound.

TABLE 42

Fiber Elasticity Conserving Guanidine Hydroxide Relaxer 13A

| Component | Relaxer 13A Wt. % |
|---|---|
| Part A: Relaxer Cream Base of Table 1 | 75.2 |
| Part B: Liquid Activator of Table 2 | 20.9 |
| Part C: MICROSIL VOLUME (as supplied) | 3.9 |

The fiber elasticity conserving guanidine hydroxide Relaxer 13A was prepared by mixing together the components shown in Table 42 substantially immediately before using on the hair. The hair relaxer procedure of Example 1 was followed except that the hair fibers were relaxed with Relaxer 13A. The wet fiber elasticity of 12 selected fibers was determined before and after relaxation measured by the ISR Method I described above and the data are shown in Table 43.

TABLE 43

ISR of Fibers Relaxed with Fiber Elasticity
Conserving Guanidine Hydroxide Relaxer 13A

| Fiber No. | ISR Value Before Relaxer 13A | ISR Value After Relaxer 13A | Calculated ISR Index |
|---|---|---|---|
| 1 | 75.17 | 47.48 | 0.63 |
| 2 | 53.85 | 36.62 | 0.68 |
| 3 | 47.53 | 21.36 | 0.45 |
| 4 | 57.20 | 38.25 | 0.67 |
| 5 | 62.35 | 41.32 | 0.66 |
| 6 | 65.54 | 43.83 | 0.67 |
| 7 | 45.51 | 30.74 | 0.68 |
| 8 | 75.59 | 51.32 | 0.68 |
| 9 | 68.08 | 31.71 | 0.47 |
| 10 | 58.94 | 33.60 | 0.57 |
| 11 | 57.27 | 39.66 | 0.69 |
| 12 | 60.19 | 37.00 | 0.61 |
| Average | 60.60 | 37.74 | 0.62 |
| S.D. | 9.49 | 8.01 | 0.08 |
| COV (%) | 15.65 | 21.22 | 13.50 |

A statistical analysis of the data conducted using Independent T-test showed that, on average, the increased wet fiber elasticity of the hair relaxed with Relaxer 13A (ISR Index: 0.62) was significantly greater than the wet fiber elasticity of hair relaxed with comparative Relaxer 1A of Example 1 (ISR Index: 0.40) at p=0.000. The % loss in wet fiber elasticity relative to that of the comparative Relaxer 1A was reduced by Relaxer 13A from 60% to about 38%.

Example 14. Fiber Elasticity Conserving Alkali Metal Hydroxide Relaxer

This example illustrates the amelioration in loss of wet hair fiber elasticity during hair relaxation with an alkali metal hydroxide, (lye-type), relaxer having about 2 to 2.5% sodium hydroxide when a combination of a hair fiber elasticity conserving agent, proproxytetramethyl piperidinyl dimethicone (PPDM), and at least one quaternary ammonium compound was present.

A lye-type, sodium hydroxide Relaxer 14A was prepared containing MICROSIL VOLUME at a concentration, as supplied, of about 12.8% as shown in Table 43. MICROSIL VOLUME was supplied as an aqueous, o/w submicron emulsion comprising about 20% medium viscosity Propoxytetramethyl Piperidinyl Dimethicone (DIMETHI-SIL-MV) and about 5% Cetrimonium Chloride. Thus, the concentration used, as supplied, provided about 2.6% active PPDM and about 0.6% quaternary ammonium compound.

TABLE 43

Fiber Conserving Sodium Hydroxide Hair Relaxer 14A with
Propoxytetramethyl piperidinyl dimethicone (PPDM)

| Ingredient (Common/Tradename/INCI Name) | % Weight (As supplied) Relaxer 14A |
|---|---|
| 1. Petrolatum | 23 |
| 2. Mineral oil | 13.5 |
| 3. Emulsifying wax N.F. | 11 |
| 4. LANETH-15 | 1 |
| 5. PEG-75-LANOLIN | 0.5 |
| 6. Water to 100% | q.s. |
| 7. Propylene glycol | 2 |
| 8. Sodium hydroxide | 2.2 |
| 9. MICROSIL VOLUME (as supplied) | 12.8 |

Relaxer 14A was prepared generally following the procedure of Example 4, except that after the oil phase and water phase were mixed together to form the emulsion, the emulsion was cooled to a temperature of about 55° C. and the fiber elasticity agent (ingredient 9) was added and mixed for about 5 minutes before proceeding with the further cooling step and addition of the sodium hydroxide.

The hair relaxer procedure of Example 4 was followed except that the hair fibers were relaxed with Relaxer 14A. The wet fiber elasticity of 12 selected fibers was determined before and after relaxation measured by the ISR Method I described above and the data are shown in Table 44.

TABLE 44

ISR Data for Fibers Relaxed with Fiber Elasticity
Conserving Sodium Hydroxide Relaxer 14A

| Fiber No. | ISR Value Before Relaxer 14A | ISR Value After Relaxer 14A | Calculated ISR Index |
|---|---|---|---|
| 1 | 72.40 | 59.78 | 0.83 |
| 2 | 43.76 | 36.39 | 0.83 |
| 3 | 66.00 | 62.39 | 0.95 |
| 4 | 60.53 | 48.10 | 0.79 |
| 5 | 60.42 | 46.25 | 0.76 |
| 6 | 60.84 | 42.90 | 0.70 |
| 7 | 70.39 | 60.42 | 0.86 |
| 8 | 58.72 | 35.73 | 0.61 |
| 9 | 55.44 | 45.20 | 0.81 |
| 10 | 53.65 | 50.92 | 0.95 |
| 11 | 71.34 | 54.05 | 0.76 |
| 12 | 63.15 | 42.27 | 0.67 |
| Average | 61.39 | 48.70 | 0.79 |
| S.D. | 8.21 | 9.02 | 0.10 |
| COV (%) | 13.37 | 18.52 | 12.84 |

A statistical analysis of the data conducted using Independent T-Test showed that, on average, the increased wet fiber elasticity of Relaxer 14A (ISR Index: 0.79) was significantly greater than the wet fiber elasticity of the comparative Relaxer 4A of Example 4 (ISR Index: 0.63) at p=0.002. The % loss in wet fiber elasticity relative to that of the comparative Relaxer 4A was reduced by Relaxer 14A from 37% to about 21%. The data also indicated that the presence of at least one quaternary compound beneficially increased the fiber elasticity conserving effectiveness of the medium viscosity PPDM in a lye type relaxer.

Example 15. Fiber Elasticity Conserving Guanidine Hydroxide Relaxer

This example illustrates the amelioration in loss of wet hair fiber elasticity during hair relaxation with a no-lye type, guanidine hydroxide when a combination of a hair fiber elasticity conserving agent, proproxytetramethyl piperidinyl dimethicone (PPDM) and more than one quaternary ammonium compound was present.

A no-lye type, guanidine hydroxide Relaxer 15A was prepared containing MICROSIL FINISH at a concentration, as supplied, of about 3.9% as shown in Table 45. MICROSIL FINISH is the tradename for a material having the INCI name: Propoxytetramethyl Piperidinyl Dimethicone (and) Cetrimonium Chloride (and) Cetrimonium Bromide (and) Trideceth-6 (and) C11-C15 Pareth-7. MICROSIL FINISH was supplied as an aqueous, submicron emulsion comprising about 12% high viscosity Propoxytetramethyl Piperidinyl Dimethicone (MICROSIL HNH-HV), about 10% cetrimonium chloride, and about 9% cetrimonium bromide. Thus, the concentration used, as supplied, provided about 0.5% active PPDM, 0.4% cetrimonium chloride; and about 0.4% cetrimonium bromide.

TABLE 45

Fiber Elasticity Conserving Guanidine Hydroxide Relaxer 15A

| Component | Relaxer 15A Wt. % |
| --- | --- |
| Part A: Relaxer Cream Base of Table 1 | 75.2 |
| Part B: Liquid Activator of Table 2 | 20.9 |
| Part C: MICROSIL FINISH (as supplied) | 3.9 |

The fiber elasticity conserving guanidine hydroxide Relaxer 15A was prepared by mixing together the components shown in Table 45 substantially immediately before using on the hair. The hair relaxer procedure of Example 1 was followed except that the hair fibers were relaxed with Relaxer 15A. The wet fiber elasticity of 12 selected fibers was determined before and after relaxation measured by the ISR Method I as described above and the data are shown in Table 46.

TABLE 46

ISR of Fibers Relaxed With Fiber Elasticity Conserving Guanidine Hydroxide Relaxer 15A

| Fiber No. | ISR Value Before Relaxer 15A | ISR Value After Relaxer 15A | Calculated ISR Index |
| --- | --- | --- | --- |
| 1 | 54.16 | 28.72 | 0.53 |
| 2 | 67.09 | 46.79 | 0.70 |
| 3 | 53.45 | 28.09 | 0.53 |
| 4 | 62.66 | 36.39 | 0.58 |
| 5 | 52.85 | 23.89 | 0.45 |
| 6 | 57.69 | 23.62 | 0.41 |
| 7 | 57.54 | 35.43 | 0.62 |
| 8 | 61.25 | 31.31 | 0.51 |
| 9 | 72.78 | 46.34 | 0.64 |
| 10 | 52.60 | 27.56 | 0.52 |
| 11 | 57.80 | 32.83 | 0.57 |
| 12 | 48.47 | 36.18 | 0.75 |
| Average | 58.20 | 33.10 | 0.57 |
| S.D. | 6.55 | 7.31 | 0.09 |
| COV (%) | 11.26 | 22.09 | 16.32 |

A statistical analysis of the data, conducted using Independent T-Test, showed that, on average, the increased wet fiber elasticity of Relaxer 15A (ISR Index: 0.57) was significantly greater than the fiber elasticity of the comparative Relaxer 4A of Example 4 (ISR Index: 0.63) at p=0.001. The % loss in wet fiber elasticity relative to that of the comparative Relaxes 4A was reduced from 60% to about 43%.

Example 16. Fiber Elasticity Conserving Alkali Metal Hydroxide Relaxer

This example illustrates the amelioration in loss of wet hair fiber elasticity during hair relaxation with an alkali metal hydroxide, (lye-type), relaxer 16A having about 2 to 2.5% sodium hydroxide when a combination of a hair fiber elasticity conserving agent, proproxytetramethyl piperidinyl dimethicone (PPDM), and more than one quaternary ammonium compound was present.

A lye-type, sodium hydroxide Relaxer 16A was prepared containing MICROSIL FINISH at a concentration, as supplied, of about 12.8%, as shown in Table 47. MICROSIL FINISH was supplied as an aqueous, submicron o/w emulsion comprised of about 12% high viscosity Propoxytetramethyl Piperidinyl Dimethicone (MICROSIL HNH HV), about 10% cetrimonium chloride, and about 9% cetrimonium bromide. Thus, the concentration used, as supplied, provided about 1.5% active PPDM, 1.3% cetrimonium chloride and about 1.2% cetrimonium bromide.

TABLE 47

Fiber Elasticity Conserving Sodium Hydroxide Hair Relaxer 16A

| Ingredient (Common/Trade/ INCI Name) | % Weight (As supplied) Relaxer 16A |
| --- | --- |
| 1. Petrolatum | 23 |
| 2. Mineral oil | 13.5 |
| 3. Emulsifying wax N.F. | 11 |
| 4. LANETH-15 | 1 |
| 5. PEG-75-LANOLIN | 0.5 |
| 6. Water to 100% | q.s. |
| 7. Propylene glycol | 2 |
| 8. Sodium hydroxide | 2.2 |
| 9. MICROSIL FINISH (as supplied) | 12.8 |

Relaxer 16A was prepared generally following the procedure of Example 4, except that after the oil phase and water phase were mixed together to form the emulsion, the sodium hydroxide was added the alkaline emulsion and cooled to a temperature of about 30° C. and the fiber elasticity agent (ingredient 9) was added and mixed for about 5 minutes.

The hair relaxer procedure of Example 4 was followed except that the hair fibers were relaxed with Relaxer 16A. The fiber elasticity of 12 selected fibers was determined before and after relaxation measured by the ISR Method I at 100% RH as described above and the data are shown in Table 48.

TABLE 48

ISR Data for Fibers Relaxed with Fiber Elasticity Conserving Relaxer 16A

| Fiber No. | ISR Value Before Relaxer 16A | ISR Value After Relaxer 16A | Calculated ISR Index |
| --- | --- | --- | --- |
| 1 | 61.37 | 56.78 | 0.93 |
| 2 | 68.08 | 50.61 | 0.74 |
| 3 | 53.62 | 47.05 | 0.88 |
| 4 | 57.09 | 51.32 | 0.90 |
| 5 | 53.56 | 32.30 | 0.60 |
| 6 | 75.44 | 55.24 | 0.73 |
| 7 | 56.38 | 50.23 | 0.89 |
| 8 | 74.49 | 69.14 | 0.93 |
| 9 | 53.82 | 48.50 | 0.90 |
| 10 | 58.22 | 51.69 | 0.89 |
| 11 | 47.31 | 44.30 | 0.94 |
| 12 | 54.22 | 42.93 | 0.79 |
| Average | 59.47 | 50.01 | 0.84 |
| S.D. | 8.80 | 8.80 | 0.10 |
| COV (%) | 14.79 | 17.60 | 12.25 |

A statistical analysis of the data conducted using Independent T-Test showed that, on average, the increased fiber elasticity of hair relaxed with Relaxer 16A (ISR Index: 0.84) was significantly greater than the fiber elasticity of hair relaxed with the comparative Relaxer 4A of Example 4 (ISR Index: 0.63) at p=0.000. The % loss in wet fiber elasticity relative to that of the comparative Relaxer 4A was reduced from 37% to about 16%.

Example 17. Fiber Elasticity Conserving Alkali Metal Hydroxide Relaxer

This example illustrates the amelioration in loss of hair fiber elasticity as reflected in post-relaxation grooming after hair relaxation with a lye-type, sodium hydroxide relaxer having about 2 to 2.5% sodium hydroxide when a hair fiber elasticity conserving agent, proproxytetramethyl piperidinyl dimethicone (PPDM) was present at an active concentration of about 1%. Hair relaxer compositions were prepared using either a low viscosity grade, i.e., DIMETHISIL HNH-LV (Relaxer 17B) or a high viscosity grade, i.e., DIMETHISIL HNH-HV (Relaxer 17C), or no fiber elasticity agent (comparative Relaxer 17A), as shown in Table 49.

TABLE 49

Sodium Hydroxide Hair Relaxers

| Ingredient (Common/Trade/ INCI Name) | % Weight (As supplied) Relaxer 17A | % Weight (As supplied) Relaxer 17B | % Weight (As supplied) Relaxer 17C |
|---|---|---|---|
| 1. Petrolatum | 23 | 23 | 23 |
| 2. Mineral oil | 13.5 | 13.5 | 13.5 |
| 3. Emulsifying wax N.F. | 11 | 11 | 11 |
| 4. LANETH-15 | 1 | 1 | 1 |
| 5. PEG-75-LANOLIN | 0.5 | 0.5 | 0.5 |
| 6. Water to 100% | q.s. | q.s. | q.s. |
| 7. Propylene glycol | 2 | 2 | 2 |
| 8. Sodium hydroxide | 2.2 | 2.2 | 2.2 |
| 9. DIMETHISIL HNH-LV | None | 0.97 | None |
| 10. DIMETHISIL HNH -HV | None | None | 0.97 |

The comparative sodium hydroxide relaxer (Relaxer 17A) was prepared following the procedure of Example 4. Relaxer 17B and Relaxer 17C, each were prepared generally following the procedure of Example 4 except that after the oil phase and water phase were mixed together to form the emulsion, and after the addition of the sodium hydroxide, the alkaline emulsion was cooled to a temperature of about 30° C. and the fiber elasticity agent (ingredient 9 or 10) was added and mixed for about 5 minutes.

A set of four hair tresses per relaxer were relaxed separately with each of Relaxers 17A, 17B and 17C. The hair relaxer procedure described in the Relaxer/ISR Method IA was generally followed, except that no ISR measurements were made; 16 grams of relaxer was applied to 4-gram, 7-inch tresses; and after the shampoo step, the shampooed tresses were allowed to dry and equilibrate overnight at ambient room temperature and ambient relative humidity of about 65%. Each of the relaxed tresses was then subjected to multiple brushing by the device and the method described in Method II to assess dry fiber breakage. Each tress first received 400 strokes, and the number of broken fibers collected underneath the tress together with any broken fibers that remained tangled with the brush were counted. Each tress was then subjected to further multiple strokes of incremental amounts of 400 strokes up to a total of 3600 brush strokes, with the number of broken fibers collected and counted at each incremental interval of 400 strokes. The 3600 brush strokes represent approximately three years of grooming damage from repeated brushing. The results are shown in Table 50.

TABLE 50

Fiber Breakage Upon Repeated Brushing of Hair Tresses Relaxed with Relaxers 17A, 17B and 17C

| Tress No. | Number of Brush Strokes | Relaxer 17A | Relaxer 17B | Relaxer 17C |
|---|---|---|---|---|
| 1 | 400 | 95 | 13 | 24 |
| 1 | 800 | 33 | 21 | 13 |
| 1 | 1200 | 27 | 48 | 11 |
| 1 | 1600 | 29 | 27 | 6 |
| 1 | 2000 | 24 | 26 | 6 |
| 1 | 2400 | 42 | 79 | 14 |
| 1 | 2800 | 21 | 81 | 16 |
| 1 | 3200 | 67 | 73 | 31 |
| 1 | 3600 | 31 | 23 | 33 |
| 2 | 400 | 57 | 34 | 27 |
| 2 | 800 | 12 | 5 | 14 |
| 2 | 1200 | 20 | 27 | 7 |
| 2 | 1600 | 10 | 26 | 1 |
| 2 | 2000 | 17 | 32 | 3 |
| 2 | 2400 | 28 | 55 | 9 |
| 2 | 2800 | 17 | 53 | 18 |
| 2 | 3200 | 46 | 56 | 47 |
| 2 | 3600 | 41 | 42 | 38 |
| 3 | 400 | 61 | 14 | 27 |
| 3 | 800 | 36 | 39 | 25 |
| 3 | 1200 | 29 | 64 | 29 |
| 3 | 1600 | 25 | 50 | 18 |
| 3 | 2000 | 15 | 38 | 12 |
| 3 | 2400 | 41 | 49 | 33 |
| 3 | 2800 | 72 | 38 | 45 |
| 3 | 3200 | 90 | 59 | 44 |
| 3 | 3600 | 60 | 39 | 43 |
| 4 | 400 | 19 | 33 | 52 |
| 4 | 800 | 17 | 11 | 51 |
| 4 | 1200 | 26 | 8 | 13 |
| 4 | 1600 | 27 | 14 | 7 |
| 4 | 2000 | 5 | 12 | 6 |
| 4 | 2400 | 22 | 28 | 12 |
| 4 | 2800 | 32 | 58 | 38 |
| 4 | 3200 | 72 | 37 | 46 |
| 4 | 3600 | 48 | 32 | 44 |
| Total Broken Fibers | | 1314 | 1344 | 853 |
| Average Broken Fibers | | 36.5 | 37.3 | 23.7 |

The number of broken fibers for each relaxer procedure was statistically analyzed using Tukey Test. The results showed that, on average, the amount of broken hair fibers from hair relaxed with Relaxer 17C (average: 23.7 fibers) was significantly less than the amount of broken hair fibers relaxed with Relaxer 17B (average: 37.3 fibers) and the comparative Relaxer 17A (average: 36.5 fibers). The amelioration of loss of fiber elasticity achieved with the high viscosity form of the fiber elasticity conserving agent, DIMETHISIL HNH-HV, was judged as providing significantly stronger relaxed hair fibers representing significantly longer life after repeated brushing equivalent to about a three-year hair grooming period. After 1200 brush strokes, which simulates about a one-year period, the average number of broken fibers were 79.3 after Relaxer 17B and 73.3 after Relaxer 17C, whereas the average number of broken fibers were 108 after the comparative Relaxer 17A. Thus, the fiber elasticity conserving effectiveness of PPDM, present at an active concentration of about 1.4% and about 3% during the hair relaxation process was discernible within the simulated practical post-relaxation period of about one year.

Example 18. Fiber Elasticity Conserving Guanidine Hydroxide Relaxer

This example illustrates the amelioration in loss of hair fiber elasticity as reflected in post-relaxer grooming after hair relaxation with a no-lye type, guanidine hydroxide relaxer containing a hair fiber elasticity conserving agent, proproxytetramethyl piperidinyl dimethicone (PPDM), present at an active concentration of about 1.5% and about 3% during the hair relaxation process.

Hair relaxer cream base compositions were prepared using either a high viscosity grade, i.e., DIMETHISIL HNH-HV at about 3.8% (Relaxer 18B) or a low viscosity grade, i.e., DIMETHISIL HNH-LV at about 1.8% (Relaxer 18C), or no fiber elasticity agent (comparative Relaxer 18A), as shown in Table 51.

TABLE 51

No-Lye Type Relaxer Cream Base

| Ingredient (Common/Trade/ INCI Name) | Weight % (As Supplied) Relaxer Cream Base 18A (Comparative) | Weight % (As Supplied) Relaxer Cream Base 18B | Weight % (As Supplied) Relaxer Cream Base 18C |
|---|---|---|---|
| Phase A. | | | |
| 1. Petrolatum | 23 | 23 | 23 |
| 2. Mineral oil | 13.5 | 13.5 | 13.5 |
| 3. Emulsifying Wax NF | 11 | 11 | 11 |
| 4. LANETH-15 | 1 | 1 | 1 |
| Phase B. | | | |
| 5. PEG-75-LANOLIN | 0.5 | 0.5 | 0.5 |
| 6. Water | 35 | 31.2 | 33.3 |
| 7. Propylene glycol | 2 | 2 | 2 |
| Phase C. | | | |
| 8. Calcium hydroxide | 5.5 | 5.5 | 5.5 |
| 9. Water | 8.5 | 8.5 | 8.5 |
| Phase D. | | | |
| 10. DIMETHISIL HNH-LV | None | None | 1.8 |
| 11. DIMETHISIL HNH-HV | None | 3.8 | None |

The relaxer cream base compositions of Table 51 were prepared as follows: oil phase A was prepared containing ingredients 1-4, heated to a range of 78-80° C.; water phase B was separately prepared containing ingredients 5-7 heated to a range of 78-80° C., mixing each phase until homogeneous. The oil phase A was then added to the water phase B at a temperature of 78-80° C., and mixed together with stirring agitation for about 15 minutes using a LIGHTENING mixer. The resulting emulsion was then cooled to a temperature of about 50° C. Aqueous phase C of ingredients 8 and 9 was prepared and added to the emulsion and homogeneously mixed. The batch was then cooled to a temperature of about 30° C., phase D was added and the batch cooled under stirring agitation using a sweep mixer (KITCHEN AID mixer) to form a cream base. The cream base was then manually homogenized using a hand held homogenizer.

The guanidine hydroxide relaxer was prepared by manually mixing together a Relaxer Cream portion A and Liquid Activator portion B at a ratio of 3.78:1 substantially immediately before using on hair to provide comparative Relaxer 18A, and fiber elasticity conserving Relaxers 18B and 18C as shown in Table 52. Thus, the active concentration of PPDM in the Relaxer 18B was about 3% and in the Relaxer 18C was about 1.4% at the time of use on the hair.

TABLE 52

Composition of Relaxers 18A, 18B and 18C

| Component in Mixture | % Weight Relaxer 18A | % Weight Relaxer 18B | % Weight Relaxer 18C |
|---|---|---|---|
| A: Relaxer Cream Base 18A of Table 51 | 79.1 | — | — |
| A: Relaxer Cream Base 18B of Table 51 | — | 79.1 | — |
| A: Relaxer Cream Base 18C of Table 51 | — | — | 79.1 |
| B: Liquid Activator of Table 2 | 20.9 | 20.9 | 20.9 |

The hair relaxing and brushing procedure described in Example 17 was repeated, except that a set of three tresses/relaxer was relaxed with either comparative Relaxer 18A, or fiber elasticity conserving Relaxer 18B or Relaxer 18C and the number of broken fibers counted after multiple brushing of 400, 800 and 1200 strokes, to approximate a one year grooming period. The brushing results are shown in Table 53.

TABLE 53

Fiber Breakage Upon Repeated Brushing of Hair Tresses Relaxed with Relaxers 18A, 18B and 18C

| Tress No. | Number of Brush Strokes | Relaxer 18A | Relaxer 18B | Relaxer 18C |
|---|---|---|---|---|
| 1 | 400 | 89 | 67 | 88 |
| 1 | 800 | 24 | 44 | 47 |
| 1 | 1200 | 18 | 73 | 79 |
| 2 | 400 | 79 | 8 | 153 |
| 2 | 800 | 39 | 52 | 57 |
| 2 | 1200 | 17 | 8 | 27 |
| 3 | 400 | 74 | 19 | 55 |
| 3 | 800 | 46 | 29 | 61 |
| 3 | 1200 | 26 | 11 | 41 |

TABLE 53-continued

Fiber Breakage Upon Repeated Brushing of Hair
Tresses Relaxed with Relaxers 18A, 18B and 18C

| Tress No. | Number of Brush Strokes | Relaxer 18A | Relaxer 18B | Relaxer 18C |
|---|---|---|---|---|
| 4 | 400 | 116 | 21 | 69 |
| 4 | 800 | 89 | 34 | 54 |
| 4 | 1200 | 174 | 37 | 87 |
| Total Broken Fibers | | 791 | 403 | 818 |
| Average Broken Fibers | | 65.9 | 33.6 | 68.2 |

Hair relaxed with Relaxer 18B had the least amount of broken fibers (average 33.6) and the amount was judged significantly lower than the amount of broken fibers (average 65.9) from the hair relaxed with the comparative Relaxer 18A, at p=0.043, when statistically analyzed by Independent T-Test. Thus, the high-viscosity form of the fiber elasticity conserving agent, present at a concentration of about 3.8% in the relaxer cream base, representing about 3% active PPDM in Relaxer 18B, effectively ameliorated loss of fiber elasticity from guanidine hydroxide relaxer.

Example 19. IN VIVO Evaluations of Fiber Elasticity Conserving Relaxers

This example illustrates in vivo evaluations of hair relaxation with either a no-lye type, guanidine hydroxide relaxer or a lye type sodium hydroxide relaxer containing a hair fiber elasticity conserving agent compared against counterpart comparative relaxers containing no hair fiber elasticity conserving agent.

A series of comparative in vivo evaluations were conducted in a salon facility with human subjects having naturally curly hair using the following half-head procedure.

The subject's hair was parted front to back to provide a left side section and a right side section so that one side could be relaxed with a hair fiber elasticity conserving hair relaxer and the opposing side could be relaxed with a counterpart comparative relaxer (containing no hair fiber elasticity conserving agent), On each selected side section, a sufficient amount of hair relaxer cream to coat the hair was applied to thinly parted sections of hair beginning with the hair section in the back (nape) of the head working downwards from the crown area and then proceeding similarly with the hair section in the front (forehead) of the head. The coated hair was physically smoothed using the back of a rattail comb, again working from nape to forehead. Approximately 90 grams of relaxer cream was applied per side for retouching new hair growth but as much relaxer cream as deemed needed to coat the hair was used. As will be appreciated by those skilled in the art, under practical salon conditions, the amount of relaxer cream applied necessarily will be varied and adjusted according to the volume of hair to be straightened on the person's head. The application time was approximately 20 minutes.

During the relaxation procedure the comfort level of the relaxer cream on the subject's scalp was evaluated on a scale of 1 to 5 where 1=severe irritation; 2=moderate irritation; 3=mild irritation; 4=minor irritation; and 5=comfortable.

After the desired level of straightening was achieved, the hair was washed with water rinsing to remove the relaxer cream and the ease of wet combing and sensory properties (tactile softness) of the water-washed hair evaluated. The water-rinsed hair was then shampooed with a non-conditioning neutralizing shampoo of Example 1, Table 4, and the degree of straightening was visually evaluated on a scale of 1 to 5 where 1=insufficient; 2=very textured; 3=textured; 4=straight; and 5=bone straight. The hair was then heat-dried and evaluated for easy dry combing, for lack of static, and for no reversion of the degree of straightening where the evaluators used a scale of 1 to 5 where 1=strongly disagree; 2=disagree; 3=neutral; 4=agree; and 5=strongly agree. The evaluators were three professional beauticians.

Evaluation Series I. No-Lye Type, Guanidine Hydroxide Relaxers.

In vivo comparative half-head evaluations, A-D, of hair relaxation with no-lye type, guanidine hydroxide relaxers were conducted using as the comparative relaxer cream, a conventional, non-conditioning composition (Sensitive Scalp Relaxer) of the type shown in Example 1A, Table 3, on one side of the person's head and one of the following relaxer compositions on the opposite side.

| Evaluation | A Composition of | No. of Subjects |
|---|---|---|
| A | Example 7A, Table 24 | 11 |
| B | Example 2A, Table 6 | 6 |
| C | Example 11A, Table 37 | 6 |
| D | Example 3A, Table 10 | 3 |
| Total | | 26 |

PPDM was the fiber elasticity conserving agent present at a concentration of about 1% in the compositions of Evaluations A, C, and D, and at about 2% in the composition of Evaluation B. On average, the results showed that the compositions of Evaluations A-D were generally judged at parity with the effective straightening and desirable sensory attributes of the comparative composition.

Evaluation Series II. Lye-Type, Sodium Hydroxide Relaxers.

In vivo comparative half-head evaluations, A-C, of hair relaxation with lye-type, sodium hydroxide relaxers were conducted using as the comparative relaxer cream, a conventional, non-conditioning composition of the type shown in Example 4A, Table 14, on one side of the person's head and one of the following relaxer compositions on the opposite side.

| Evaluation | A Composition of | No. of Subjects |
|---|---|---|
| A | Example 9A, Table 31 | 6 |
| B | Example 12A, Table 39 | 4 |
| C | Example 16A, Table 47 | 4 |
| Total | | 14 |

PPDM was the fiber elasticity conserving agent present at a concentration of about 1% in the compositions of Evaluations A and B, and at about 1.5% in the composition of Evaluation C. On average, the results showed that the compositions of Evaluations A-C were generally at parity with the effective straightening and desirable sensory attributes of the comparative composition.

Overall, the results showed that desirable straightening effectiveness of a no-lye type, guanidine hydroxide relaxer or a lye type sodium hydroxide relaxer was maintained during in vivo hair relaxation with compositions containing the PPDM hair fiber elasticity conserving agent. The results also showed that desirable beneficial sensory properties of the compositions were maintained.

Example 20. In Vivo Evaluations of Fiber Elasticity Conserving Relaxers

This example illustrates in vivo amelioration of hair fiber loss during hair relaxation with a no-lye type, guanidine hydroxide relaxers containing a hair fiber elasticity conserving agent, proproxytetramethyl piperidinyl dimethicone (PPDM) of medium viscosity, present at an active concentration of about 3% in the relaxer during the hair relaxation process, compared against counterpart comparative relaxers containing no hair fiber elasticity conserving agent.

Hair relaxer cream base compositions were prepared using a medium viscosity grade, i.e., DIMETHISIL HNH-MV at about 3.8% (Relaxer 20B) or no fiber elasticity agent (comparative Relaxer 20A) as shown in Table 54. The cream base compositions were prepared by the procedure described in Example 18.

TABLE 54

No-Lye Type Relaxer Cream Base

| Ingredient (Common/Trade/ INCI Name) | Weight % (As Supplied) Relaxer Cream Base 20A (Comparative) | Weight % (As Supplied) Relaxer Cream Base 20B |
|---|---|---|
| Phase A. | | |
| 1. Petrolatum | 23 | 23 |
| 2. Mineral oil | 13.5 | 13.5 |
| 3. Emulsifying Wax NF | 11 | 11 |
| 4. LANETH-15 | 1 | 1 |
| Phase B. | | |
| 5. PEG-75-LANOLIN | 0.5 | 0.5 |
| 6. Water | 35 | 31.2 |
| 7. Propylene glycol | 2 | 2 |
| Phase C. | | |
| 8. Calcium hydroxide | 5.5 | 5.5 |
| 9. Water | 8.5 | 8.5 |
| Phase D. | | |
| 10. DIMETHISIL HNH-MV | None | 3.8 |

The guanidine hydroxide relaxer was prepared by manually mixing together a Relaxer Cream portion A and Liquid Activator portion B at a ratio of 3.78:1 substantially immediately before using on hair to provide comparative Relaxer 20A, and fiber elasticity conserving Relaxer 20B as shown in Table 55. The active concentration of PPDM in Relaxer 20B was about 3% at the time of use on the hair.

TABLE 55

Composition of Relaxers 20A and 20B

| Component in Mixture | % Weight Relaxer 20A | % Weight Relaxer 20B |
|---|---|---|
| A: Relaxer Cream Base 20A of Table 54 | 79.1 | — |
| A: Relaxer Cream Base 20B of Table 54 | — | 79.1 |
| B: Liquid Activator of Table 2 | 20.9 | 20.9 |

A series of comparative in vivo evaluations were conducted in a salon facility with five human subjects having naturally curly hair generally following the half-head procedure described in Example 19 so that the hair on one side could be relaxed with hair fiber elasticity conserving hair Relaxer 20B and the opposing side could be relaxed with comparative Relaxer 20A (containing no hair fiber elasticity conserving agent). The applied Relaxer remained in contact with the hair for about 18 minutes.

After the desired level of straightening was achieved, the hair was washed for about 3 to 5 minutes with water rinsing to remove the relaxer. The water-rinsed hair was then shampooed with a non-conditioning neutralizing shampoo of Example 1, Table 4, a conventional, commercial conditioner (AFFIRM FIBERGUARD Sustenance, Avlon Industries Inc.) was applied to the shampooed hair and left in contact with the hair for about 10 minutes, and then removed by water rinsing the hair. For each side of the head hair, the rinsed hair was detangled using a comb having widely spaced teeth and broken hair strands removed by the wide-tooth comb were collected, then the hair was combed again using a rat-tail type comb having medium to finely spaced teeth and hair strands removed by the comb were collected. The combed-out hair strands collected were then pooled, allowed to air dry, and weighed on a precision (four-digit) weighing balance. The gram weight of the collected, pooled combed-out hair per side is shown in Table 56 for comparative Relaxer 20A and fiber elasticity conserving Relaxer 20B.

TABLE 56

Gram Weight of Combed-out Hair

| Subject No. | Relaxer 20A | Relaxer 20B |
|---|---|---|
| 1 | 0.0257 | 0.0261 |
| 2 | 0.1619 | 0.1131 |
| 3 | 0.3721 | 0.3307 |
| 4 | 0.1375 | 0.1153 |
| 5 | 0.0962 | 0.0809 |
| Average Weight | 0.1587 | 0.1332 |

The average loss of hair during combing from the comparative Relaxer A was 0.1587 grams and from the fiber elasticity conserving Relaxer B was 0.1332. Hair relaxed with Relaxer 20B had the least amount of broken fibers and the amount was judged significantly lower than the amount of broken fibers from the hair relaxed with the comparative Relaxer 20A, at $p=0.046$, when the mean values were statistically analyzed by Paired T-Test. A decrease in the amount of broken fibers was judged to represent conservation of wet fiber elasticity. Thus, the medium-viscosity form of the fiber elasticity conserving agent, present at a concentration of about 3.8% in the relaxer cream base, representing about 3% active PPDM in Relaxer 20B, effectively ameliorated loss of wet fiber elasticity from guanidine hydroxide relaxer.

The scope of the invention should not be limited by the preferred embodiments set forth in the examples but should be given the broadest interpretation consistent with the description as a whole. The claims are not to be limited to the preferred or exemplified embodiments of the invention.

What is claimed is:

1. An aqueous hair relaxer composition having an alkalinity of at least pH 12, the composition comprising an active hair straightening ingredient in a cosmetically acceptable vehicle and a fiber elasticity conserving amount of at least one hair fiber elasticity conserving polyorganosiloxane compound having at least one siloxyl unit substituted with a pendant side chain comprising a 2,2,6,6-tetramethylpiperidinyl group attached to the silicon as represented by general Formula (I)

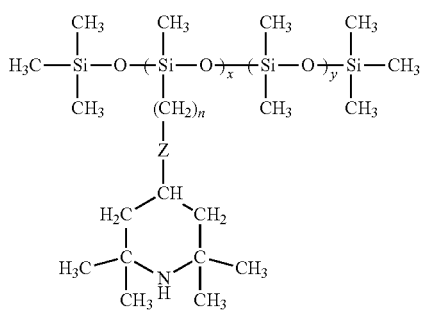 (I)

where the average value of x and y each is independently 1 to about 200; n is 0, 1, 2 or 3; and Z is a heteroatom or substituted heteroatom, selected from the group consisting of O, NR, where R is H or alkyl, and S.

2. The composition of claim 1, wherein n is 3 and Z is O.

3. The composition of claim 1, wherein the polyorganosiloxane is present in an amount of about 0.1 to about 4 percent by weight, based on the weight of the hair relaxer composition applied to the hair.

4. The composition of claim 1, wherein the composition has a pH value of 12 to about 14.

5. The composition of claim 1, wherein the active hair straightening ingredient is an alkali metal hydroxide selected from the group consisting of sodium hydroxide, potassium hydroxide and lithium hydroxide.

6. The composition of claim 1, wherein the active hair straightening ingredient is a strong organic base selected from the group consisting of guanidine compounds and derivatives thereof.

7. The composition of claim 6, wherein the organic base is selected from the group consisting of guanidine, guanidine hydroxide, and water-soluble alkaline guanidine salts.

8. The composition of claim 6, wherein the organic base is generated in situ from a mixture of an alkaline earth hydroxide and an alkaline salt of the organic base.

9. The composition of claim 8, wherein the alkaline earth hydroxide is calcium hydroxide and the salt is guanidine carbonate.

10. The composition of claim 1, wherein the polyorganosiloxane is propyloxytetramethyl piperidinyl dimethicone.

11. The composition of claim 10, wherein the propyloxytetramethyl piperidinyl dimethicone is in the form of a submicron emulsion.

12. The composition of claim 11, wherein the submicron emulsion comprises at least one quaternary ammonium compound.

13. A method of ameliorating loss of hair fiber elasticity during straightening of human hair in a hair relaxing step with an aqueous hair relaxer composition having a pH of at least 12 comprising an active alkaline hair straightening ingredient, wherein the method comprises using an aqueous hair relaxer composition of claim 1 in the hair relaxing step.

14. The method of claim 13, wherein the polyorganosiloxane compound is propyloxytetramethyl piperidinyl dimethicone.

* * * * *